(12) United States Patent
Schmees et al.

(10) Patent No.: US 7,388,006 B2
(45) Date of Patent: Jun. 17, 2008

(54) NON-STEROIDAL PROGESTING

(75) Inventors: Norbert Schmees, Berlin (DE); Manfred Lehmann, Berlin (DE); Ulrike Fuhrmann, Berlin (DE); Peter Muhn, Berlin (DE); Christa Hegele-Hartung, Muelheim/Ruhr (DE); Michael Klotzbuecher, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 221 days.

(21) Appl. No.: 10/384,775

(22) Filed: Mar. 11, 2003

(65) Prior Publication Data

US 2003/0232824 A1    Dec. 18, 2003

Related U.S. Application Data

(60) Provisional application No. 60/363,044, filed on Mar. 11, 2002.

(30) Foreign Application Priority Data

Mar. 11, 2002    (EP) .................... 02005530

(51) Int. Cl.
*A61K 31/502* (2006.01)
*A61K 31/536* (2006.01)
*C07D 237/32* (2006.01)
*C07D 265/02* (2006.01)

(52) U.S. Cl. .............. 514/230.5; 514/248; 514/259; 514/361; 514/362; 544/63; 544/237; 548/126; 548/260; 548/261

(58) Field of Classification Search .......... 514/230.5, 514/248, 259, 361, 362; 544/63, 237; 548/126, 548/260, 261
See application file for complete search history.

(56) References Cited

U.S. PATENT DOCUMENTS 6,344,454 B1 * 2/2002 Lehmann et al. ........ 514/230.5

FOREIGN PATENT DOCUMENTS

WO      WO98/54159      * 12/1998

* cited by examiner

Primary Examiner—James O. Wilson
Assistant Examiner—Paul V. Ward
(74) Attorney, Agent, or Firm—Millen, White, Zelano, Branigan, P.C.

(57) ABSTRACT

The present invention relates to non-steroidal progestins of the general formula (I)

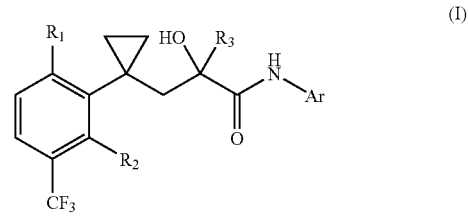

wherein
$R_1$ and $R_2$ are independently of each other —H or —F,
$R_3$ is —$CH_3$ or —$CF_3$, and Ar is

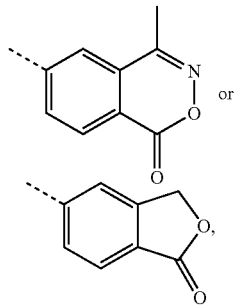

(a)

(b)

or a pharmaceutically acceptable derivative or analogue thereof. These progestins are suitable for selectively modulating progesterone receptor mediated effects in different target tissues, particularly in uterine tissue versus breast tissue. Therefore, the progestins of the present invention, optionally in combination with estrogens, may be used for contraception (in particular in estrogen-free oral contraceptives), hormone replacement therapy and the treatment of gynecological disorders. The present invention furthermore relates to methods for selectively modulating progesterone receptor mediated effects in different target tissues or organs.

26 Claims, 4 Drawing Sheets

NON-STEROIDAL PROGESTING

This application claims the benefit of the filing date of U.S. Provisional Application Ser. No. 60/363,044 filed Mar. 11, 2002.

FIELD OF THE INVENTION

The present invention relates to non-steroidal progestins of the general formula (I) as well as to uses of said compounds for selectively modulating progesterone receptor mediated effects in different target tissues, i.e., to progestins having a dissociated activity profile regarding different target tissues, preferably a uterus/breast dissociated profile. The present invention further relates to uses of said compounds as well as to methods for selectively enhancing progesterone receptor mediated effects in uterine tissue with respect to progesterone receptor mediated effects in breast tissue. Due to the unique dissociated activity and selectivity profile of the progestins according to the present invention, the invention in particular relates to the use of said compounds for fertility control, in particular for oral contraception, hormone replacement therapy and the treatment of gynecological disorders. The progestins according to the present invention are especially suitable for use in estrogen-free oral contraceptives.

BACKGROUND OF THE INVENTION

Progesterone is a unique reproductive hormone, and it plays a decisive role for tissues of female reproduction. Its principal target organs are uterus, ovary, breast and the hypothalamus-pituitary axis. In addition to the primary use as pregnancy control for women (e.g., oral contraception (OC)), progestins, optionally combined with estrogens, are widely used in hormone replacement therapy (HRT). Progestins are also used to treat several gynecological disorders, e.g., dysmenorrhea, endometriosis, and dysfunctional uterine bleeding caused by hormonal deficiency or imbalance. Due to certain effects of progestins, which may be undesirable for some applications, or cross-reactivities with receptors other than the progesterone receptor, the development of new generations of progestins to improve their activity profile has been a great challenge. Additionally, the exploration of therapeutic applications such as oncology demands progestins with new activity profiles.

Recently, non-steroidal progestins with a very strong affinity to the progesterone receptor, but with additional androgen activity were disclosed in WO 98/54159. These progestins are not only suitable for female fertility control (FC) and HRT (optionally in combination with estrogens), but may also be used for male FC, male HRT and for treating andrological syndromes.

WO 00/32584 discloses specific non-steroidal glucocorticoids exhibiting a clear dissociation between anti-inflammatory activity and metabolic effects, while their progestagenic potential is less pronounced although their affinity for the progesterone receptor is high.

Finally, DE 100 38 639.3 discloses glucocorticoids exhibiting a strong affinity for the glucocorticoid receptor and having thus anti-inflammatory as well as additional anti-allergic, immunosuppressive and anti-proliferative activity for treating diseases including arthritis, allergies etc.

However, in particular in the area of female FC and HRT there is a strong need for progestins having low affinity for other hormone receptors, but exhibiting instead a strong dissociation between different PR target tissues or organs, such as in the breast and in the reproductive tract.

In particular, the provision of a dissociated progestin with an antiproliferative potential in the breast tissue and, at the same time, beneficial effects in the endometrium seems desirable, as there is a number of epidemiological studies about the relation between breast cancer incidence and use of combined oral contraceptives (COCs) or HRT, especially with respect to extended periods of use (see e.g., K. E. Malone et al., Epidemiologic Reviews 1993, 15, 80-97 and Standford et al., Epidemiologic Reviews 1993, 15, 98-107). Although the risks are contradictory and controversial, there is evidence that many years of intake under certain circumstances might enhance the mitotic activity of normal breast epithelial cells. Therefore, a dissociated activity profile of progestins regarding the provision of beneficial, e.g. antiproliferative, effects in the breast, but with the classical progestagenic effects in the ovary and/or uterus is desirable.

Recently, assays for screening for progesterone receptor ligands exhibiting tissue-specificity have been provided, cf. PCT/EP01/15200 (U.S. Pat. No. 60/305,875). One approach of screening for progesterone receptor (PR) ligands with a dissociated activity profile was based on the fact that the PR is expressed in two different isoforms (PR-A and PR-B) which seem to be capable of being activated independently of each other by compounds having a selectivity for either PR-A or PR-B.

Both PR-isoforms are expressed in all progesterone target organs tested so far (e.g. breast, uterus). However, there is strong evidence that PR-A and PR-B function in a tissue-specific manner to mediate responses to progesterone. Isoform-specific knock-out mice show different functions of PR-A and PR-B in the same target organ. Based on these studies, PR-B seems to be the most responsible receptor for mammary gland proliferation and differentiation, whereas the antiproliferative action of progestins on the uterine epithelium and on ovulation is most likely mediated by PR-A (B. Mulac-Jericevic, Science 2000, 289, 1751-1754; Orla Conneely, Endocrine Society Meeting, Toronto, June 2000).

Thus, the invention disclosed in PCT/EP1/15200 was based on the new theory that isoform-specific ligands of PR activity may allow tissue-selective modulation of progestin activity in hormonal therapy and contraception. However, while PCT/EP01/15200 (U.S. Ser. No. 60/305,875) provided a tool for identifying potentially PR-isoform and/or tissue-specific PR ligands, the present invention provides specific non-steroidal progestins exhibiting pronounced PR isoform selectivity as well as a surprising dissociated effect on different PR target organs, in particular a uterus/breast dissociated activity profile.

OBJECTS OF THE INVENTION

As outlined above, one object of the present invention is to provide novel progestins for use in FC, HRT, and the treatment of gynecological disorders. Another object is to provide novel progestins that are suitable for use in estrogen-free oral contraceptives. In particular, it is desired to provide novel progestins exerting beneficial effects on certain PR target organs, such as the uterus, and not enhancing undesired effects on other PR target organs, such as proliferation/differentiation of the mammary epithelium. Thus, it is desired to provide novel progestins that exhibit a dissociated activity profile regarding different target tissues or organs, preferably uterus/breast specific progestins.

A further object of the present invention is to provide a method for selectively modulating progesterone mediated effects in a first selected tissue, preferably uterine tissue, with respect to a second selected tissue, preferably breast tissue. It is particularly desirable to provide a method for selectively enhancing antiproliferative effects in the uterus while preventing undesirable effects, such as proliferation and differentiation, in breast tissue.

Another object of the present invention is to provide PR isoform selective (preferably PR-A versus PR-B selective) progestins. It is also desired to provide methods for selectively modulating PR isoform, preferably PR-A, mediated effects, as well as for selectively activating PR isoform, preferably PR-A, transcription.

All these objects are surprisingly achieved by the provision of progestins of the general formula (I), the uses of said progestins as well as the methods for modulating progesterone mediated effects according to the present invention as described in further detail below.

SUMMARY OF THE INVENTION

In a first aspect, the present invention provides a compound of the general formula (I) as identified below. The preferred compound according to the present invention is (+)-5-{2-hydroxy-3-[1-(2-fluoro-5-trifluoromethylphenyl)-cyclopropyl]-2-trifluoromethyl-propionylamino}-phthalide.

In a second aspect, the present invention provides a pharmaceutical composition comprising a compound of the general formula (I), either alone (for example in an estrogen-free oral contraceptive) or optionally combined with 17α-ethinyl estradiol or another estrogen as a further component.

In a third aspect, the present invention provides a compound of the general formula (I) for use in therapy.

In a fourth aspect, the present invention provides a pharmaceutical composition comprising a compound of general formula (I) for use in therapy.

In a fifth aspect, the present invention provides the use of a compound of general formula (I) or of a pharmaceutical composition comprising said compound for the manufacture of a medicament for selectively modulating progesterone receptor mediated effects in a first selected tissue, preferably uterine tissue, with respect to a second selected tissue, preferably breast tissue, in particular for use in fertility control, hormone replacement therapy or the treatment of gynecological disorders.

In a sixth aspect, the present invention provides the use of a compound of general formula (I) as a contraceptive, preferably an estrogen-free oral contraceptive, such as, for example, the "progesterone-only pill" (POP).

In a seventh aspect, the present invention provides a method for selectively modulating progesterone receptor mediated effects in a first selected tissue, preferably uterine tissue, with respect to a second selected tissue, preferably breast tissue, in particular for use in fertility control, hormone replacement therapy or the treatment of gynecological disorders, the method comprising the step of administering to an individual a compound of general formula (I).

Furthermore, in an eighth aspect, the present invention provides the use of a compound of general formula (I) for the manufacture of a medicament for selectively activating progesterone receptor isoform A transcription with respect to progesterone receptor isoform B transcription as well as for selectively enhancing progesterone receptor isoform A mediated effects with respect to progesterone receptor isoform B mediated effects.

In a ninth aspect, the present invention provides a method for selectively activating progesterone receptor isoform A transcription with respect to progesterone receptor isoform B transcription as well as for selectively enhancing progesterone receptor isoform A mediated effects with respect to progesterone receptor isoform B mediated effects.

DETAILED DESCRIPTION OF THE INVENTION

Figure 1:
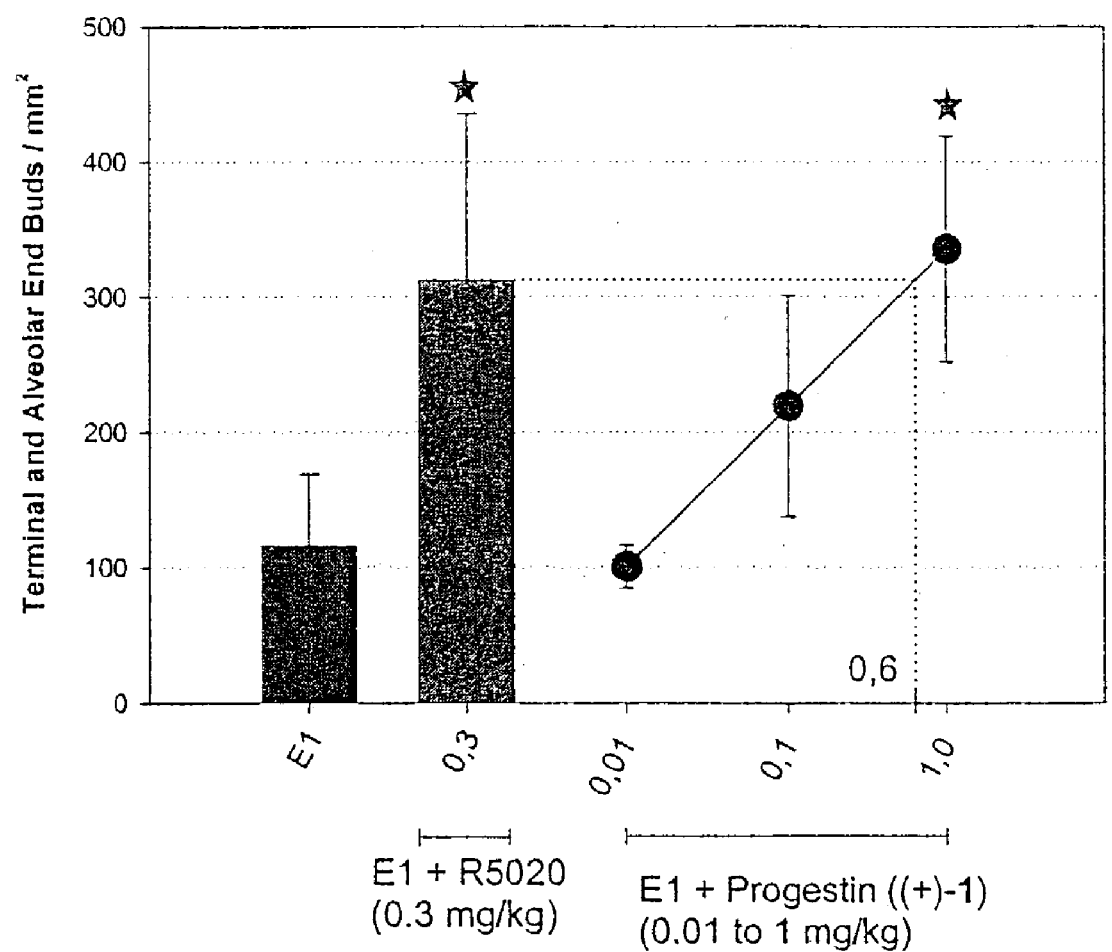
FIG. 1 demonstrates the differences in the stimulation of terminal and alveolar endbud formation effected by compound ((+)-1) compared to the standard progestin promegestone (R5020) after subcutaneous application in immature ovariectomized female rats (equi-efficient dose of ((+)-1) with respect to 0.3 mg/kg R5020).

In a first aspect, the present invention provides non-steroidal progestagenic compounds of the general formula (I)

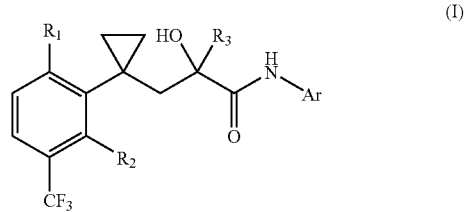

wherein $R_1$ and $R_2$ are independently of each other —H or —F,
$R_3$ is —$CH_3$ or —$CF_3$, and
Ar is

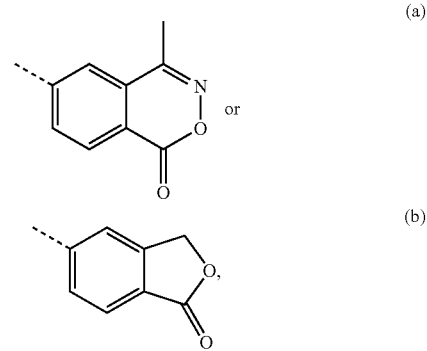

or a pharmaceutically acceptable derivative or analogue thereof, with the proviso that the compound is not 5-[3-{1-(3-trifluoromethylphenyl)-cyclopropyl}-2-hydroxy-2-trifluoromethylpropionylamino]-phthalide.

For the purposes of the present invention, a "pharmaceutically acceptable derivative or analogue" of the compound of the general formula (I) as depicted above is a compound whose structure is derived from and/or is essentially similar to the structure of general formula (I) as shown above and whose biological activity (in vitro and/or in vivo) is also essentially similar to that achieved, with a compound of general formula (I) in qualitative and/or quantitative terms.

As the compounds of general formula (I) exhibit a stereogenic center, they exist in two different stereoisomeric (enantiomeric) forms. Thus, the compounds according to the present invention may be provided as racemates, i.e., mixtures of enantiomers (identified for example by (±)). However, e.g. by means of enantioselective synthesis or by applying standard separation methods as described e.g. in Example 1a) below, the compounds of the present invention may also be provided as the separate (+) or (−), i.e. dextrorotatory or laevorotatory, enantiomers. It is to be understood that by disclosing the (+) or (−) enantiomers, also the inherent absolute configurations of these enantiomers are disclosed.

Standard separation methods are within the purview of a skilled person. For example, racemates may be separated by chromatography on an optically active carrier (e.g., CHIRALPAK AD™) into the pure isomers. Furthermore, it is also possible to react the free hydroxy group of the (racemic) compounds of formula (I) with an optically active acid (e.g. α-hydroxyphenylacetic acid, camphorsulfonic acid or tartaric acid), resulting in diastereomeric esters, which may be separated by fractional crystallization or by chromatography and subsequently saponified to form the optically pure enantiomers.

The preferred compounds of the present invention are the compounds of general formula (I) as depicted above in the form of the (+)-enantiomer.

Examplary compounds of general formula (I) are the following:

Racemic, (+) and (−)-5-{2-hydroxy-3-[1-(2-fluoro-5-trifluoromethylphenyl)-cyclopropyl]-2-trifluoromethyl-propionylamino}-phthalide (((±)-1), ((+)-1) and ((−)-1)), racemic, (+) and ((±)-6-{2-hydroxy-3-[1-(2-fluoro-3-trifluoromethylphenyl)-cyclopropyl]-2-trifluoromethyl-propionylamino}-4-methyl-2,3-benzoxazi-1-one (((±)-2), ((+)-2) and ((−)-2)), racemic, (+) and (−)-6-{2-hydroxy-3-[1-(3-trifluoromethylphenyl)-cyclopropyl]-2-methyl-propionylamino}-4-methyl-2,3-benzoxazin-1-one (((±)-3), ((+)-3) and ((−)-3)), racemic, (+) and (−)-5-{2-hydroxy-3-[1-(2-fluoro-3-trifluoromethylphenyl)-cyclopropyl]-2-trifluoromethyl-propionylamino}-phthalide (((±)-4), ((+)-4) and ((−)-4)), racemic, (+) and (−)-6-{2-hydroxy-3-[1-(2-fluoro-5-trifluoromethylphenyl)-cyclopropyl]-2-trifluoromethyl-propionylamino}-4-methyl-2,3-benzoxazin-1-one (((±)-5), ((+)-5) and ((−)-5)), and racemic, (+) and (−)-6-{2-hydroxy-3-[1-(2-fluoro-5-trifluoromethylphenyl)-cyclopropyl]-2-methyl-propionylamino}-4-methyl-2,3-benzoxazin-1-one (((±)-6), ((+)-6) and ((−)-6)).

Particularly preferred compounds according to the present invention are the following:
((±)-1), ((+)-1), ((−)-1),
((±)-2), ((+)-2), ((−)-2),
((±)-3), ((+)-3), ((−)-3),
((±)-4), ((+)-4) and ((−)-4)).

The most preferred compound of the present invention is 5-{2-hydroxy-3-[1-(2-fluoro-5-trifluoromethylphenyl)-cyclopropyl]-2-trifluoromethyl-propionylamino}-phthalide, hereinafter designated as compound (1):

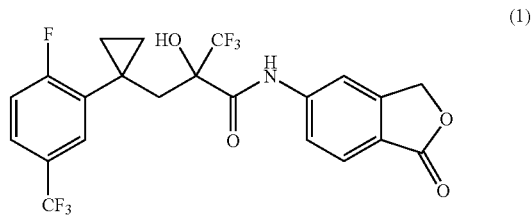

As mentioned above, the (+)-enantiomer of 5-{2-hydroxy-3-[1-(2-fluoro-5-trifluoromethylphenyl)-cyclopropyl]-2-trifluoromethyl-propionylamino}-phthalide is particularly preferred and designated ((+)-1). The synthetic route to (+)-5-{2-hydroxy-3-[1-(2-fluoro-5-trifluoromethylphenyl)-cyclopropyl]-2-trifluoromethyl-propionylamino}-phthalide ((+)-1) as well as physical data of this compound are outlined in Example 1. Experimental results obtained for this compound in in vivo as well as in vitro tests are described in Examples 2, 3, 4 and 5.

From these examples it is evident that the preferred progestin ((+)-1) according to the present invention exhibits ideal in vitro and in vivo profiles. Regarding the in vitro profile of compound ((+)-1), it is demonstrated in Example 5 below that compound ((+)-1) is a selective PR-A agonist and exhibits a high PR-A versus PR-B specificity (details regarding the PR isoform specificity of the compounds according to the present invention are given with respect to the eighth and ninth aspect of the invention described below). As it is demonstrated, compound ((+)-1) selectively activates PR-A transcription and thus selectively enhances PR-A mediated effects.

Regarding the in vivo activity profile of compound ((+)-1), it is to be described as being highly dissociated. Specifically, ((+)-1) exhibits a very high activity at the uterus in maintaining pregnancy, and a considerably lower activity at the mammary gland, i.e., ((+)-1) does not activate proliferation and differentiation of the mammary gland (cf. Example 3 for rat), especially in the dose range where maintenance of pregnancy is achieved.

Compound ((+)-1) is one of the most potent progestins in vivo identified so far. In the ovulation inhibition test (cf. Example 2), compound ((+)-1) is at least as potent as the standard progestin used in this test, R5020 (promegestone). In the pregnancy maintenance test in rat (cf. Example 3), compound ((+)-1) is about 10 times more potent than levonorgestrel (LNG). Furthermore, in the Clauberg test (endometrial transformation in rabbit; cf. Example 4), an identical progestagenic potency for ((+)-1) was recorded upon subcutaneous and oral application. This demonstrates that ((+)-1) is highly active when administered orally.

Furthermore, compound ((+)-1) exhibits no androgenic as well as no anti-androgenic activity in vivo although it exhibits moderate binding affinity for the androgen receptor (AR). The absence of androgenic as well as anti-androgenic activity in vivo was confirmed by tests performed with orchidectomized rats (change in prostate weight and in the seminal vesicle). In a pregnancy maintenance test performed with rats, even in a dose which is 100 times higher than the dose required for maintaining pregnancy, no androgenic activity of compound ((+)-1) is encountered. Additionally, although compound ((+)-1) was found to have a very high affinity for the glucocorticoid receptor (GR), it does not seem to exhibit any glucocorticoid or any anti-glucocorticoid activity in vivo, which was concluded from experiments directed to changes in thymus weight. Finally, since compound ((+)-1) binds to the mineralocorticoid receptor (MR) and the estrogen receptor-α (ERα) with negligible affinity in vitro, no MR or ERα hormonal effects are to be expected from interaction with these receptors.

Regarding its above-described effects and activity, compound ((+)-1) is to be regarded as exemplary for all other compounds of general formula (I) according to the present invention.

Due to the above-demonstrated advantageous effects of the novel progestins according to the present invention, in particular (+)-5-{2-hydroxy-3-[1-(2-fluoro-5-trifluoromethylphenyl)-cyclopropyl]-2-trifluoromethyl-propionylamino}-phthalide, i.e., compound ((+)-1), these progestins are especially suitable for use in contraceptives, in particular in estrogen-free oral contraceptives, such as, for example, the progestin-only pill (POP).

In a second aspect, the present invention provides a pharmaceutical composition comprising a progestin of general formula (I) as defined above, with the proviso that the compound is not 5-[3-{1-(3-trifluoromethylphenyl)-cyclopropyl}-2-hydroxy-2-trifluoromethylpropionylamino]-phthalide. Preferred pharmaceutical compositions are those comprising the preferred compounds as mentioned above. A more preferred pharmaceutical composition according to the present invention comprises 5-{2-hydroxy-3-[1-(2-fluoro-5-trifluoromethylphenyl)-cyclopropyl]-2-trifluoromethyl-propionyl-amino}-phthalide (1), most preferably (+)-5-{2-hydroxy-3-[1-(2-fluoro-5-trifluoromethylphenyl)-cyclopropyl]-2-trifluoromethyl-propionyl-amino}-phthalide ((+)-1).

Depending on the desired application regarding e.g. the condition to be treated/influenced or the mode of application, the pharmaceutical composition according to this invention may—when not used as an estrogen-free oral contraceptive (which is one of the preferred uses of the progestins according to the present invention)—in addition to a compound of general formula (I), preferably compound ((+)-1), comprise an estrogen component. For example, in case the pharmaceutical composition is intended to be used for (oral) contraception (which use will be explained in more detail below), suitable estrogens are those that are commonly used in combined (oral) contraceptives. Although any natural estrogen (in particular estriol or estradiol) or synthetic estrogen, steroidal or non-steroidal, may be used, the preferred estrogen in this respect, in particular for oral administration, is 17α-ethinyl estradiol as well as esters, ethers and other derivatives of 17α-ethinyl estradiol.

Furthermore, estratriene-3-amidosulfonate (WO 96/05216 and WO 96/05217), derived from estradiol or ethinyl estradiol, may be used in combination with compounds of general formula (I), preferably compound ((+)-1). Also 14α,15α-methylene steroids derived from estrane, in particular 14α,15α-methylene-17α-estradiol as well as the corresponding 3-amidosulfonate derivatives are suitable in this respect.

For use in hormone replacement therapy (which use will be explained in more detail below), the estrogen to be optionally combined with a progestin of general formula (I) according to the present invention, preferably compound ((+)-1), is preferably estradiol, estradiol valerate or other esters of estradiol as well as conjugated (natural, e.g. equine) estrogens.

In a pharmaceutical composition according to the present invention, the compound as defined by the general formula (I) above, preferably compound ((+)-1), and optionally an additional estrogen component, preferably 17α-ethinyl estradiol, has/have to be present in a (pharmaceutically) effective amount. The amount to be administered (i.e., a "(pharmaceutically) effective amount") varies within a broad range and depends on the condition to be treated or any other desired use and the mode of administration. It can cover any amount efficient for the intended treatment or use. Determining a "pharmaceutically effective amount" is within the purview of the person skilled in the art.

More precisely, in a pharmaceutical composition according to the present invention for any of the envisaged uses (i.e., for oral contraception (combined oral contraceptives as well as estrogen-free oral contraceptives, such as, for example, the "progestin-only pill"), HRT and the treatment of gynecological disorders as well as other disease conditions) a daily dose of a compound of general formula (I), preferably compound ((+)-1), to be administered to an individual in the range of 0.01 to 2 mg is considered generally appropriate. However, doses which are especially suitable for specific applications are as follows:

In case the progestin according to the present invention, preferably compound ((+)-1), is to be used in a pharmaceutical composition as a combined oral contraceptive, in combination with an estrogen component as defined above, a suitable daily dose to be administered to an individual is 10 μg to 100 mg. A preferred daily dose to be administered to an individual in this respect is 10 μg to 1 mg.

In case the progestin according to the present invention, preferably compound ((+)-1), is to be used in a pharmaceutical composition as an estrogen-free oral contraceptive, such as a "progestin-only pill" (POP) without any additional estrogen component, a suitable daily dose to be administered to an individual is 10 μg to 1 mg, preferably 30 μg to 300 μg or 10 μg to 100 μg, while also a range of as low as 1 μg to 10 μg may be applicable.

In case the progestin according to the present invention, preferably compound ((+)-1), is to be used in a pharmaceutical composition for HRT, a suitable daily dose to be administered to an individual is 10 μg to 10 mg, preferably 10 μg to 1 mg (corresponding to 1/100 of the equi-efficient dose of medroxyprogesterone acetate (MPA)), most preferably 10 μg to 100 μg.

In case the progestin of the present invention, preferably compound ((+)-1), is to be used in a pharmaceutical composition for applications other than contraception or HRT, i.e., in the treatment of gynecological disorders, such as premenstrual syndrome (which manifests itself trough headache, signs of depression, water retention etc.), dysmenorrhea, endometriosis, myoma or dysfunctional uterine bleeding, the amount to be administered is generally in the same range as for the application in COCs, POPs and HRT as described above, but it may also differ from these values, depending on the effect which is intended to be achieved.

In case the progestin according to the invention, preferably compound ((+)-1), is combined in a pharmaceutical composition as defined above with an estrogen component, preferably 17α-ethinyl estradiol, the daily dose of the estrogen component to be administered to an individual is such that it is (or is equi-efficient to) 0.01 to 0.05 mg, preferably 0.015 to 0.03 mg of 17α-ethinyl estradiol.

In case the progestins according to the present invention, in particular compound ((+)-1), are administered in combination with an estrogen component, preferably 17α-ethinyl estradiol, for use as a contraceptive, preferably in a combined oral contraceptive (COC), or in HRT, the progestin and the estrogen may either be administered simultaneously, e.g. in one tablet, but they may also be administered separately according to a certain regime and even via different routes, e.g. orally and parenterally. For use in contraception (such as in estrogen-free oral contraceptives) as well as in HRT, the daily doses of the progestin according to the present invention as defined above, preferably compound ((+)-1), and optionally (in case of combined oral contraceptives) the estrogen component as defined above may stay the same over the entire female menstrual cycle or they may vary—independently of each other—over the female menstrual cycle, such as in known two—or multiple stage preparations, where the concentrations of both the progestin as well as the estrogen increase in two or more stages during the menstrual cycle. Furthermore, in a sequential application it is envisaged that in a first period of the cycle the estrogen component is administered alone and in a second period of the cycle the progestin is added. Furthermore, as it is the case in conventional oral contraceptives, the administration of the progestins of the present invention, in particular compound ((+)-1), and optionally an additional estrogen component as defined above, may be interrupted for x days after a period of intake of y=28−x days in a 28-day cycle, wherein x may be, for example, 7, 6, 5, 4 or less and thus y may be, for example, 21, 22, 23, 24 or more. In the case of estrogen-free oral contraceptives, such as, for example, POPs, no interruption of the daily administration of the progestin according to the present invention, in particular compound ((+)-1), may be envisaged.

The manufacture of the pharmaceutical compositions according to the invention may be performed according to methods known in the art and will be explained in further detail below. Commonly known and used adjuvants as well as further suitable carriers, diluents, flavorings etc. may be used, depending on the intended mode of administration as well as particular characteristics of the; active compound to be used, such as solubility, bioavailability etc. Suitable carriers and adjuvants may be such as recommended for pharmacy, cosmetics and related fields in: Ullmann's Encyclopedia of Technical Chemistry, Vol. 4, (1953), pp. 1-39; Journal of Pharmaceutical Sciences, Vol. 52 (1963), p. 918ff; H.v.Czetsch-Lindenwald, "Hilfsstoffe für Pharmazie und angrenzende Gebiete"; Pharm. Ind. 2, 1961, p.72ff; Dr. H. P. Fiedler, Lexikon der Hilfsstoffe für Pharmazie, Kosmetik und angrenzende Gebiete, Cantor KG, Aulendorf in Württemberg, 1971.

As indicated above, the preferred mode of application of the progestins of general formula (I), preferably compound ((+)-1), or of pharmaceutical compositions comprising said compound, either without (such as in estrogen-free oral contraceptives) or together with an additional estrogen component, such as 17α-ethinyl estradiol, is oral application, e.g., by tablets, pills, dragees, gel capsules, granules, solutions, emulsions or suspensions. For the preparation of pharmaceutical compositions for oral administration, the compounds suitable for the purposes of the present invention as defined above can be admixed with commonly known and used adjuvants and carriers such as for example, gum arabic, talcum, starch, sugars (such as, e.g., mannitose, methyl cellulose, lactose), gelatin, surface-active agents, magnesium stearate, aqueous or non-aqueous excipients, paraffin derivatives, cross-linking agents, dispersants, emulsifiers, lubricants, conserving agents, flavoring agents (e.g., ethereal oils) or solubility enhancers (e.g., benzyl benzoate or benzyl alcohol). In the pharmaceutical composition, the active ingredients may also be dispersed in a microparticle, e.g. a nanoparticulate, composition.

However, also other modes of application are envisaged, such as parenteral administration, e.g., intraperitoneal, intramuscular (such as by injection of aqueous, oily or other solutions, e.g. by depot injection where the hormones are released slowly into the blood from the depot and carried from there to the target organs, e.g. the hypothalamus, pituitary and uterus), subcutaneous or transdermal application. For parenteral administration, the active agents can be dissolved or suspended in a physiologically acceptable diluent, such as, e.g., oils with or without solubilizers, surface-active agents, dispersants or emulsifiers. As oils for example and without limitation, olive oil, peanut oil, cottonseed oil, soybean oil, castor oil and sesame oil may be used. Transdermal application can be accomplished by suitable patches, as generally known in the art, specifically designed for the transdermal delivery of active agents, optionally in the presence of specific permeability enhancers. Furthermore, also emulsions, ointments, creams or gels may be used for transdermal delivery.

Another mode of application is by implantation of a depot implant comprising an inert carrier material, such as biologically degradable polymers or synthetic silicones such as e.g. silicone rubber. Such implants are designed to release the active agent in a controlled manner over an extended period of time (e.g., 3 to 5 years). Another suitable mode of administration is via intravaginal devices (e.g. vaginal rings) or intrauterine systems (IUS) containing reservoirs for controlled release of active agents, such as the progestins of the present invention and/or estrogens over extended periods of time. Such IUS (as, e.g., MIRENA™) is introduced into the uterine cavity where it continuously releases defined amounts of hormone for up to 5 years (or until the system is removed). The amount of progestin and/or estrogen released daily correspond to the daily doses as defined above.

In a third aspect the present invention provides a compound of the general formula (I)

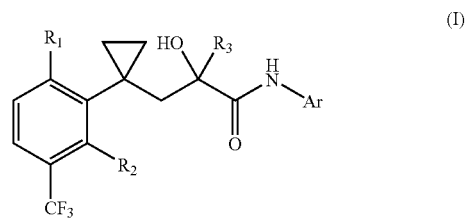

wherein $R_1$ and $R_2$ are independently of each other —H or —F, $R_3$ is —$CH_3$ or —$CF_3$, and Ar is

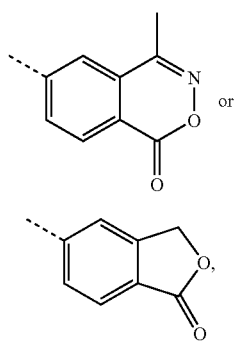

(a)

(b)

or a pharmaceutically acceptable derivative or analogue thereof, with the proviso that the compound is not 5-[3-{1-(3-trifluoromethylphenyl)-cyclopropyl}-2-hydroxy-2-trifluoromethylpropionylamino]-phthalide, for use in therapy.

The present invention in a fourth aspect furthermore provides a pharmaceutical composition comprising a compound of the general formula (I) as defined above with the proviso that the compound is not 5-[3-{1-(3-trifluoromethylphenyl)-cyclopropyl}-2-hydroxy-2-trifluoromethylpropionylamino]-phthalide, for use in therapy.

Preferred compounds and compositions for use in therapy according to the third and fourth aspects of the present invention are identical to the preferred compounds and compositions already described above with respect to the first and second aspect of the invention. Preferably, the compounds and compositions according to the present invention, in particular compound ((+)-1) or a pharmaceutical composition comprising compound ((+)-1), are for use in fertility control, e.g. as (combined) oral contraceptives (COC), estrogen-free oral contraceptives, such as, for example, the progestin-only "minipills" (POPs), contraceptive patches, injections, implants or intrauterine systems (IUS), or for use in hormone replacement therapy or the treatment of gynecological disorders, such as dysmenorrhea, endometriosis, myoma, premenstrual syndrome, dysfunctional uterine bleeding etc., optionally in combination with estrogens, in particular 17α-ethinyl estradiol. Further explanations regarding conditions to be treated or other applications, e.g. in the area of contraception, will be discussed below with respect to the fifth and sixth aspect of the present invention.

In a fifth aspect, the present invention provides the use of a compound of general formula (I)

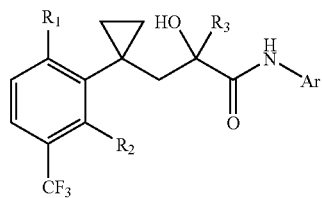

(I)

wherein $R_1$ and $R_2$ are independently of each other —H or —F, $R_3$ is —$CH_3$ or —$CF_3$, and Ar is

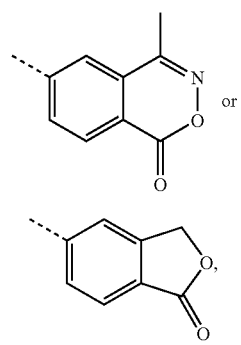

(a)

(b)

or a pharmaceutically acceptable derivative or analogue thereof, however including the compound 5-[3-{1-(3-trifluoromethylphenyl)-cyclopropyl}-2-hydroxy-2-trifluoromethyl-propionylamino]-phthalide excluded in the first, second, third and fourth aspects of this invention from the meanings of the general formula (I), for the manufacture of a medicament for selectively modulating progesterone receptor mediated effects in a first selected target tissue with respect to a second selected target tissue.

Also for the fifth aspect of the present invention, the same compounds of general formula (I) as depicted above are preferred compounds for the purposes of the present invention as already disclosed for the previous aspects, in particular for the first aspect, of the present invention. Thus, compound (1), in particular compound ((+)-1), i.e., (+)-5-{2-hydroxy-3-[1-(2-fluoro-5-trifluoromethylphenyl)-cyclopropyl]-2-trifluoromethyl-propionylamino}-phthalide, or a pharmaceutically acceptable derivative or analogue thereof, is the most preferred compound also for the purposes of the fifth aspect of the present invention.

"Selective modulation" of PR mediated effects for the purposes of this aspect of the present invention means that the compound of general formula (I) as defined above achieves one or more effect(s) in a first selected target tissue which is/are of a different kind (e.g., inhibiting, stimulating or not affecting) and/or of a different intensity (e.g., weaker or stronger and/or pertaining longer or shorter) compared to the effect(s) induced by said ligand in a second selected target tissue.

It is to be understood that the benefits of the present invention are of course not limited to a first and second selected tissue per se, but are in the same way directed to a first and second selected organ so that the fifth aspect of this invention also pertains to the use of a compound as defined above by formula (I) (and including the compound 5-[3-{1-(3-trifluoromethylphenyl)-cyclopropyl}-2-hydroxy-2-trifluoromethyl-propionyl-amino]-phthalide excluded in the first, second, third and fourth aspects of this invention from the meanings of the general formula (I)) for the manufacture of a medicament for selectively modulating PR mediated effects in a first selected target organ with respect to a second selected target organ. For the purposes of the present invention, the first selected target organ is preferably the reproductive tract, i.e., mainly the uterus, and the second selected target organ is the breast, in particular the mammary gland. Accordingly, the first selected target tissue is preferably uterine tissue and the second selected target tissue is preferably breast tissue.

Thus, the compounds according to the fifth aspect of the present invention exhibit a dissociated activity profile with respect to the first selected target tissue, preferably uterine tissue, and a second (i.e., different) selected target tissue, preferably breast tissue.

Preferably, "selectively modulating PR mediated effects in the first selected target tissue with respect to the second selected target tissue" in the specific context of the present invention means selectively enhancing PR mediated effects in said first selected tissue, preferably uterine tissue, with respect to PR mediated effects in said second selected tissue, preferably breast tissue. In other words, by the uses and methods of the present invention, PR mediated effects in the first selected tissue (preferably uterine tissue) are selectively enhanced relative (i.e., compared) to the PR mediated effects in the second selected tissue (preferably breast tissue), i.e., a dissociation regarding PR mediated effects in said first and second selected target tissues is observed.

The term "selectively enhancing PR mediated effects in a first selected tissue with respect to PR mediated effects in a second selected tissue" is thus not intended to be limited to any absolute values of PR mediated effects in the first and second selected tissues, but covers scenarios wherein, for example, the PR mediated effect induced in the second selected tissue (preferably breast tissue) is low or not detectable at all, and the PR mediated effect induced in the first selected tissue (preferably uterine tissue) is very pronounced or only moderate, but in any case enhanced with respect to the PR mediated effect induced in the second selected tissue.

Most preferably, the compounds according to the present invention as defined above for the fifth aspect of this invention exert beneficial and/or protective PR mediated effects in the reproductive tract, such as the maintenance of pregnancy, and also maintain classical progestational effects, such as ovulation inhibition etc. with respect to undesired PR mediated effects in the breast, such as proliferation/differentiation of the mammary epithelium. Thus, the compounds according to the present invention exhibit a very high activity at the uterus and a relatively lower activity at the mammary gland.

Thus, the present invention provides progestagenic compounds having a clearly dissociated progestin activity profile in that they are capable of inducing a desired, beneficial effect in one progesterone target organ, such as the uterus, while not inducing undesired effects in another progesterone target organ, e.g., the breast, such as proliferation/differentiation of the mammary tissue (which is evident by increased formation of terminal end buds in the mammary glands). However, the benefit of the present invention is not limited to a dissociated uterine/breast tissue profile, but it is equally useful for other target tissue combinations involving progesterone receptor mediation.

That the compounds of general formula (I) as defined above for this aspect of the present invention, preferably compound ((+)-1), are actually exhibiting a dissociated activity (uterus versus mammary gland) is demonstrated e.g. in Example 3 below, wherein it is confirmed that the compounds of the present invention, preferably compound ((+)-1), exhibit a strong progestational activity in vivo at the uterus regarding maintenance of pregnancy and a considerably lower progestational activity in the breast tissue regarding proliferation of terminal end buds in the mammary gland. A detailed description of the bioassays used for determining whether a certain compound actually selectively modulates PR mediated effects in a first selected tissue, preferably uterine tissue, with respect to a second selected tissue, preferably breast tissue, may also be found in the examples.

However, in general terms it can-be said that for determining whether a certain compound actually selectively modulates a defined PR mediated effect in a defined target tissue with respect to another target tissue, the type of the effect induced by said compound (i.e., whether the compound inhibits, does not influence, enhances or maintains the PR mediated effect in said target tissue) as well as the intensity of the induced effect are measured, preferably relative to the effect induced by a known "standard" PR ligand, such as the standard progestin R5020 (promegestone). Then the effects achieved in the first and second target tissue with the test compound are compared and evaluated, preferably under consideration of the desired medical indication or intended application (e.g., fertility control or HRT etc.). A detailed description of assays for screening for tissue-specific progesterone receptor ligands, based on the one hand on in vivo tests and on the other hand on in vitro tests as well as on combined in vitro/in vivo tests, is given in PCT/EP01/15200 (U.S. Pat. No. 60/305,875) whose disclosure in this respect is incorporated herein by reference. For example, suitable in vivo tests for determining whether a certain progestin selectively induces PR mediated effects in the uterus or the ovary versus the breast are a rodent bioassay on proliferation/differentiation of the mammary epithelium, a pregnancy maintenance test or an endometrium proliferation/differentiation test in rodents, and an ovulation inhibition test or a superovulation test in rodents. However, as mentioned before, the present invention is not limited to uterus/breast selective progestins, but is equally useful for other tissues or organs involving PR mediated effects. It is certainly within the skilled person's knowledge to select and perform suitable in vivo tests as defined above in certain desired target tissues other than the preferred tissues as defined above and to determine the effect induced by a certain test progestin in relation to a suitable standard progestin.

Due to the pronounced dissociated activity profile of the progestins of general formula (I) as defined above, in particular compound ((+)-1), regarding the modulation of PR mediated effects in different progesterone target organs, in particular the breast and the reproductive tract (the uterus), the medicaments prepared from the compounds of the present invention (and optionally an additional estrogen component) are suitable for treating certain gynecological disorders as well as for application in HRT. The use of the compounds according to the present invention as contraceptives is not always a purely medical indication and thus belongs to the sixth aspect of this invention and will therefore be discussed below. Gynecological disorders are to be understood to comprise for example endometriosis, myoma, dysmenorrhea, premenstrual syndrome (PMS, which is a collective term for a number of symptoms, such as lower abdominal pain, headaches, edema, depression, irritability etc. which are experienced by many women six to eight days before menstruation) and dysfunctional uterine bleeding (caused by hormonal deficiencies or imbalances), but are not limited to these. Also irregular menstrual cycles may be controlled by the compounds of the present invention. HRT is predominantly used to alleviate climacteric symptoms, such as menopausal symptoms (e.g., hot flashes, night sweats), osteoporosis, dry mucous membranes as well as psychological symptoms (e.g. depression). There is even strong evidence that HRT prevents the development of cardiovascular diseases, Alzheimer's disease, colon cancer or other diseases.

As to the envisaged as well as preferred modes of application, the envisaged as well as preferred doses, envisaged as well as preferred additional ingredients of medicaments and the optional presence of an additional estrogen component, reference is made to the second aspect of the present invention. All statements made there with respect to suitable, preferred, more preferred and most preferred embodiments equally apply to the fifth aspect of the invention, i.e. the use of the compounds of general formula (I), however including the compound 5-[3-{1-(3-trifluoromethylphenyl)-cyclopropyl}-2-hydroxy-2-trifluoromethyl-propionyl-amino]-phthalide excluded in the first, second, third and fourth aspects of this invention from the scope of general formula (I), for the manufacture of a medicament for modulating PR mediated effects in a first selected tissue with respect to a second selected tissue. Preferred embodiments of this aspect of the invention (as well as all other aspects of the present invention) are also contained in the respective dependent claims of each aspect of the invention.

Whereas the fifth aspect of the present invention relates to uses of the compounds of general formula (I) for purely medical purposes, the sixth aspect of the present invention pertains to the use of a compound of general formula (I)

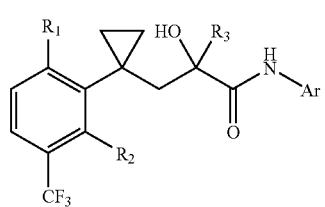

(I)

wherein $R_1$ and $R_2$ are independently of each other —H or —F,
$R_3$ is —CH$_3$ or —CF$_3$, and
Ar is

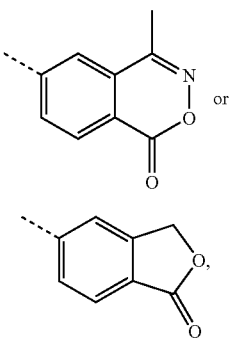

(a)

or (b)

or a pharmaceutically acceptable derivative or analogue thereof, with the proviso that the compound is not 5-[3-{1-(3-trifluoromethylphenyl)-cyclopropyl}-2-hydroxy-2-trifluoromethylpropionylamino]-phthalide, as a contraceptive.

Although fertility control in general and contraception in particular may under certain circumstances also be applied for purely medical reasons (and thus pertain in this respect to the fifth aspect of the present invention discussed above), contraception (i.e., prevention of pregnancy) is generally understood not to be intended to prevent or cure a certain disease Nevertheless, contraception using progestins either alone (as in estrogen-free oral contraceptives, for example in POPs) or in combination with estrogens (as in COCs) may also have additional beneficial (medical) effects over and above the inhibition of pregnancy. It is known that contraceptives are capable of curing certain disorders, such as abnormal bleeding pattern during the menstrual cycle or the premenstrual syndrome with the symptoms listed above with respect to the fifth aspect of the present invention. Contraceptives generally also have a positive influence on the appearance of the skin. Furthermore, women using contraceptives suffer less often from pelvic inflammatory disease (PID), and the risk of ovarian, endometrial and colorectal cancer is reduced.

As mentioned above, the novel progestins according to the present invention and preferably compound ((+)-1) are advantageously used in estrogen-free oral contraceptives, such as, for example, the progestin-only "minipill" (POP). These estrogen-free oral contraceptives are a suitable alternative for women who cannot tolerate an estrogen-progestin combination due to certain estrogen effects, but nevertheless want to enjoy the advantages of hormonal contraception in tablet form. Furthermore, estrogen-free oral contraceptives are also an option for women who are breast-feeding, since estrogens suppress milk production and therefore use of combined estrogen-progestin contraceptives is not advisable during that time.

The novel progestins according to the present invention and preferably compound ((+)-1) may not only be used in oral contraceptives that are completely free of any estrogen component, but also in oral contraceptives that are substantially free of estrogen. "Substantially free of estrogen" is to be understood as referring to amounts of estrogen that are less than what is usually contained in estrogen-progestin combined oral contraceptives.

However, in addition to the above benefits of contraceptives comprising progestins alone (i.e., as in estrogen-free oral contraceptives) or in combination with estrogens, contraceptives comprising the progestins according to the present invention as defined above, preferably compound ((+)-1), actually also avoid potential disadvantages of known contraceptives in that the progestins according to the present invention only activate the progesterone receptor at a specific target tissue or organ (in particular the uterus), but only to a lower degree (or not at all) at any other, undesired tissue or organ (in particular the mammary gland), thus rendering these treatments well tolerable and less prone to serious side effects or even the risk of inducing potential further health problems. Furthermore, due to their potential for a tailored modulation of PR mediated conditions and effects, the progestins of the present invention, in particular compound ((+)-1), may be administered in a much lower dose as a consequence of their target tissue specificity than known progestins used for contraceptives (and also for the other indications discussed with respect to the fifth aspect of the present invention). Other aspects of the use of progestins as contraceptives may be taken from the book "Kontrazeption mit Hormonen" ("Contraception with hormones") by H.-D. Taubert and H. Kuhl, Georg Thieme Verlag Stuttgart—New York, 1995.

Regarding preferred embodiments of the sixth aspect of the present invention, reference is made on the one hand to the claims and on the other hand to the explanations and descriptions given with respect to the second aspect of the present invention, namely the pharmaceutical compositions comprising the progestins of general formula (I), preferably compound ((+)-1). All that was said there with respect to modes of administration, doses, combinations of ingredients (in particular with respect to an optional additional estrogen component) and any other preferred embodiments equally applies to the sixth aspect of the invention, i.e. the use of the compounds of general formula (I) for contraception.

The seventh aspect of the present invention pertains to a method for selectively modulating progesterone receptor mediated effects in a first selected tissue or organ with respect to a second selected tissue or organ. The method comprises the step of administering an effective amount of a compound of general formula (I)

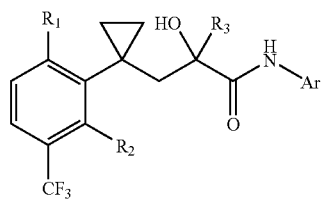
(I)

wherein $R_1$ and $R_2$ are independently of each other —H or —F,
$R_3$ is —$CH_3$ or —$CF_3$, and
Ar is

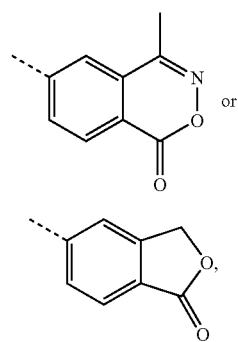

(a)

or (b)

or a pharmaceutically acceptable derivative or analogue thereof, however including the compound 5-[3-{1-(3-trifluoromethylphenyl)-cyclopropyl}-2-hydroxy-2-trifluoromethyl-propionylamino]-phthalide excluded in the first, second, third, fourth and sixth aspects of this invention from the meanings of the general formula (I), or of a pharmaceutical composition comprising such compound of general formula (I) to an individual in need of such selective modulation of progesterone receptor mediated effects.

With respect to the seventh aspect of the present invention, the selective modulation of progesterone mediated effects in a first selected tissue with respect to a second selected tissue for example comprises—as in the other aspects of the invention discussed above—selectively enhancing desired and/or protective effects in a first selected target tissue, preferably uterine tissue, or target organ, preferably the uterus, with respect to undesired PR mediated effects (such as proliferation/differentiation) in a second target tissue, preferably breast tissue, or target organ, preferably the mammary gland. However, it is to be understood that the present invention is not limited to the uterus/breast dissociated activity of the progestins according to the invention, but that the present invention also covers dissociated activities regarding any other selected first and second target tissues influenced by PR mediation. Regarding the preferred embodiments as well as a detailed explanation of the indication "modulation of PR mediated effects in a first selected tissue with respect to a second selected tissue", reference is made to the statements made above with respect to other aspects of the present invention, in particular to the fifth aspect.

As already explained with respect to the fifth aspect of the present invention as well as with respect to the sixth aspect of the present invention, an individual, preferably a mammal, most preferably a human, in need of such selective modulation of progesterone mediated effects may be, for example, a female individual needing (for medical reasons) or wishing to prevent pregnancy. Thus, as already outlined earlier, the method according to the seventh aspect of the present invention may be used for contraception. In this respect, everything that was said earlier with respect to the use of the progestins according to the present invention as contraceptives, equally applies to the method according to the seventh aspect of the invention, including preferred embodiments regarding doses, dosing regimes, modes of administration, optional combination of the progestins according to the present invention with estrogens etc.

Apart from contraception, medical indications wherein the modulation of PR mediated effects in a first tissue with respect to a second tissue is advantageous or necessary, are for example hormone replacement therapy or the treatment of gynecological disorders. All these indications have already been described in detail with respect e.g. to the fifth aspect of this invention and are equally applicable for the present seventh aspect of the invention.

The eighth and ninth aspects of the present invention relate to uses of the compounds of general formula (I),

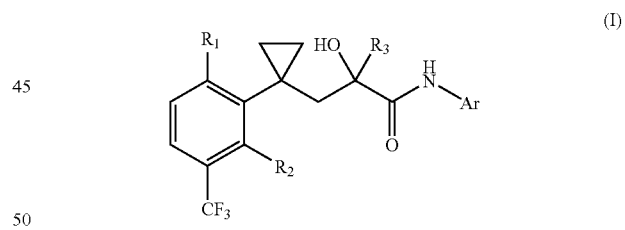
(I)

wherein $R_1$ and $R_2$ are independently of each other —H or —F,
$R_3$ is —$CH_3$ or —$CF_3$, and
Ar is

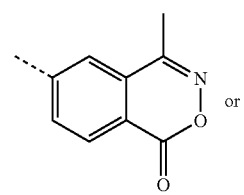

(a)

or

-continued

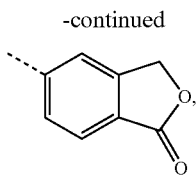

(b)

or a pharmaceutically acceptable derivative or analogue thereof, however including the compound 5-[3-{1-(3-trifluoromethylphenyl)-cyclopropyl}-2-hydroxy-2-trifluoromethyl-propionylamino]-phthalide excluded in the first, second, third, fourth and sixth aspects of this invention from the meanings of the general formula (I), for the manufacture of a medicament for selectively activating PR-A transcription with respect to PR-B transcription and for selectively enhancing PR-A mediated effects with respect to PR-B mediated effects.

The eighth and ninth aspect of the present invention also relates to methods of selectively activating PR-A transcription with respect to PR-B transcription and to methods of selectively enhancing PR-A mediated effects with respect to PR-B mediated effects, the methods comprising the step of administering a compound of general formula (I)

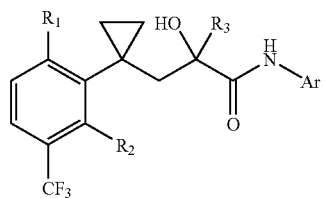

(I)

wherein $R_1$ and $R_2$ are independently of each other —H or —F,
$R_3$ is —CH$_3$ or —CF$_3$, and
Ar is

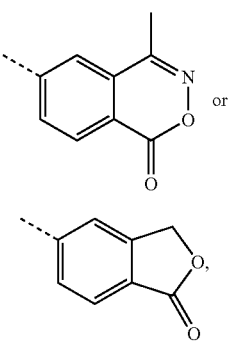

(a)

or (b)

or a pharmaceutically acceptable derivative or analogue thereof, however including the compound; 5-[3-{1-(3-trifluoromethylphenyl)-cyclopropyl}-2-hydroxy-2-trifluoromethyl-propionylamino]-phthalide excluded in the first, second, third, fourth and sixth aspects of this invention from the meanings of the general formula (I), to an individual in need of such selective modulation of PR-A transcription and of PR-A mediated effects, respectively.

As demonstrated in Example 5 below, the progestins of the present invention, in particular the compound (+)-5-{2-hydroxy-3-[(1-(2-fluoro-5-trifluoromethylphenyl)-cyclopropyl]-2-trifluoromethyl-propionylamino}-phthalide, ((+)-1), have been found to selectively activate PR-A transcription and thus to selectively induce PR-A mediated effects while preferably not influencing PR-B transcription and thus PR-B mediated effects.

As mentioned in the section "Background of the invention" above, based on studies by B. Mulac-Jericevic as well as O. Conneely, PR isoform B seems to be the most responsible receptor for mammary gland proliferation and differentiation, whereas the antiproliferative action of progestins on the uterine epithelium and on ovulation is most likely mediated by PR isoform A (B. Mulac-Jericevic, Science 2000, 289, 1751-1754; Orla Conneely, Endocrine Society Meeting, Toronto, June 2000). Thus, as outlined above, progestins exhibiting a selectivity for the progesterone isoform A, i.e. progestins that activate PR-A transcription and preferably at the same time do not influence PR-B transcription, are also likely to selectively enhance PR mediated effects in the uterus while at the same time preferably do not influence PR mediated effects in the mammary gland. The verification of this connection between PR isoform specificity and tissue selectivity of PR ligands has already been a subject of the earlier application PCT/EP01/15200 (U.S. Pat. No. 60/305,875). The present invention has again confirmed this principle by means of Examples 3 and 5, wherein e.g. the preferred compound according to the present invention, compound ((+)-1) is demonstrated to be a selective and highly potent PR-A agonist and thus exhibits a strongly dissociated activity profile in vitro with respect to the PR isoform A versus B as well as in vivo with respect to the different target tissues, inducing desired and beneficial effects in uterine tissue while not inducing undesired effects in breast tissue, such as the proliferation/differentiation of the mammary gland.

However, the applicability of the present invention is not restricted to the uterus versus breast system, but may be extended to other progesterone target organ systems. Basically any condition involving PR isoform mediated effects may be treated by the uses of the progestins of the present invention, either by the manufacture of a medicament according to the eighth aspect of this invention or by the methods comprising administering said progestins according to the ninth aspect of the present invention. It is to be understood that all statements made above with respect to other aspects of the present invention regarding the preferred progestins according to the invention, mode of administration, dose and dosing regimes, combination with other components, such as estrogens, etc. equally apply to the eighth and ninth aspects described here.

It has to be noted that for the purpose of the present invention, the selectivity (or also specificity, which term is herein also used as a synonym for selectivity) of a progestin according to the invention for PR isoform A with respect to PR isoform B is defined as a difference in transcription efficacy induced by this progestin in PR-A versus PR-B transfected cells. Preferably, this difference is above or equal to 10%, more preferably above or equal to 15% and most preferably above or equal to 20%. The "transcription efficacy" is defined as the response achieved with a defined concentration of test progestin relative to a standard progestin (e.g., R5020) in either PR-A or PR-B transfected cells.

Beside "transcription efficacy", another potential parameter for evaluating the selectivity of a test progestin with respect to either PR-A or PR-B is "potency", i.e., the EC$_{50}$ value (or its technical equivalent $ED_{50}$), determined in vitro in either PR-A or PR-B transfected cells. Preferably, the difference in potency achieved by a certain test progestin in PR-A versus PR-B transfected cells should be in the range of or above a factor of 10. Further details regarding the determination of transcription efficacy and potency may be found in Example 5 below as well as in the earlier application PCT/EP01/15200 (US No. 60/305,875) which is for this purpose herein incorporated by reference. As it is demonstrated below in Example 5, the compounds of the present invention, in particular compound ((+)-1), are strong agonists with a selectivity for PR-A.

Apart from the in vivo applications described above for the progestins according to the present invention due to their specificity for PR isoform A, this pronounced ability for selectively activating PR-A transcription may also be exploited e.g. for in vitro assays involving the two PR isoforms, either for diagnostic or for scientific purposes. Thus, the eighth and ninth aspects of the present invention also provide in vitro uses and methods, which pertain purely to the receptor level. For example, the compounds of the present invention, preferably compound ((+)-1) may be used as a standard for evaluating the PR isoform specificity potential of further PR ligands. Accordingly, the compounds of the present invention may be incorporated into diagnostic or scientific kits for determining the ability of other compounds for selectively activating PR isoform transcription. The compounds of the present invention may also be used for identifying PR isoform specific cells which may be needed for certain diagnostic or scientific applications.

Regarding details of the in vitro test for progestins having PR isoform specificity as used in Example 5 hereinbelow, it is referred to PCT/EP01/15200 (US No. 60/305,875) which is incorporated herein by reference. PCT/EP01/15200 (US No. 60/305,875) in particular discloses how cells stably transfected with either PR-A or PR-B expressing plasmids are obtained, how PR-A and PR-B transcription is detected and how those PR ligands exhibiting PR isoform specificity may be identified. Furthermore, as mentioned above, PCT/EP01/15200 (U.S. Pat. No. 60/305,875) also discloses a screening assay for tissue selective PR ligands.

Regarding a process for preparing a compound of the general formula (I)

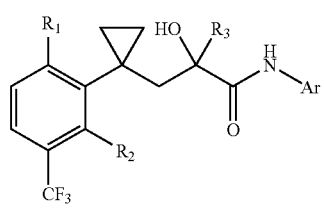

(I)

wherein
$R_1$ and $R_2$ are independently of each other —H or —F,
$R_3$ is —$CH_3$ or —$CF_3$, and Ar is

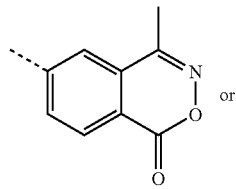
(a)

or

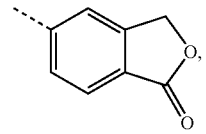
(b)

or a pharmaceutically acceptable derivative or analogue thereof, with or without the proviso that the compound is not 5-[3-{1-(3-trifluoromethylphenyl)-cyclopropyl}-2-hydroxy-2-trifluoromethylpropionylamino]-phthalide, such process is analogous to the process disclosed e.g. in WO 98/54159 for obtaining the larger class of compounds described therein. However, since the compounds of the present invention are novel with respect to the compounds disclosed in WO 98/54159, in the following several different synthetic routes for obtaining the progestins of the present invention are outlined. A detailed description of the preparation of compounds (1), (2), (3) and (4) is given in Examples 1a), 1b), 1c) and 1d), respectively.

A first method for obtaining the compounds of the general formula (I) as defined above starts with a compound of the general formula (11)

(II)

wherein the substituents $R_1$, $R_2$ and Ar are defined as explained above for general formula (I). A compound of general formula (II) is reacted with a compound of general formula $CF_3$—$SiMe_3$ or $CF_3$—$Si(R^x)_3$, wherein $R^x$ is $C_1$ to $C_4$ alkyl, in the presence of a catalyst, or with a methyl metal compound, e.g. a Grignard-type reagent or a lithium alkyl, to form a compound of the general formula (I). As catalysts, fluoride salts or basic salts such as alkaline carbonates may be used (cf. J. Am. Chem. Soc. 111, 1989, 393).

Furthermore, compounds of general formula (I) according to the present invention may also be formed from compounds of the general formul (III)

(III)

wherein R₁ and R₂ are defined as explained above for general formula (I) and LG is a leaving group, such as —Cl or —Br or a tosylate substituent. A compound of general formula (III) is reacted with a compound Ar—NH—R', wherein Ar is as defined above for general formula (1) and R' is either a hydrogen atom or a $C_1$ to $C_5$ acyl group. Under certain circumstances, substituent R' may have to be removed later. The compound of general formula (III) may also be formed as an intermediate product, for example, it can be an acid chloride formed intermediately from a corresponding carbonic acid.

The substitution pattern at the phenyl ring in general formula (I) according to the present invention and carrying the substituents $R_1$, $R_2$ and —$CF_3$ is obtained according to methods known in the art for selective substitution at an aromatic ring. The present invention is further illustrated by means of the following examples which are, however, not intended to limit the scope of the present invention.

EXAMPLES

Example 1

Preparation of Progestins of General Formula (1)

a) Preparation of (±)-, (+)- and (−)-5-{2-hydroxy-3-[1-(2-fluoro-5-trifluoro-methylphenyl)-cyclopropyl]-2-trifluoromethyl-propionylamino}-phthalide (±)-, (+)- and (−)-1):

1-(2-Fluoro-5-trifluoromethylphenyl)-cyclopropyl-carbonitrile 8.15 ml of N,N'-dimethylimidazolidinone are added at a temperature of −70° C. under an inert gas atmosphere within 10 min. to 78 ml of a 2 M lithium diisopropylamide solution (tetrahydrofurane/heptane/ethyl benzene). After 15 min., 10.6 g of (2-fluoro-5-trifluoromethylphenyl)-acetonitrile are added. After 10 min. at −20° C., 20.3 ml 1,2-dichloroethane are added (note: it is also possible to react (2-fluoro-5-trifluoromethylphenyl)-acetonitrile with 1,2-dibromoethane and $Cs_2CO_3$) and the mixture is stirred at −20° C. for 2 hours and for 16 hours at ambient temperature. Then the mixture is cooled by means of ice and a saturated solution of ammonium chloride as well as ethyl acetate are added. The ethyl acetate phase is then washed twice with saturated ammonium chloride solution and twice with water, dried over sodium sulfate, concentrated and distilled via a Kugelrohr apparatus.

Yield: 8.7 g of 1-(2-fluoro-5-trifluoromethylphenyl)-cyclopropyl-carbonitrile, b.p. 140° C./0.04 hPa.

1-(2-Fluoro-5-trifluoromethylphenyl)-cyclopropyl-carbaldehyde 8.5 g of 1-(2-fluoro-5-trifluoromethylphenyl)-cyclopropyl-carbonitrile are dissolved in 60 ml of toluene. At −70° C., 56 ml of 1 M diisobutylaluminum hydride dissolved in toluene are added within 45 min. After 4 hours, at −78° C., 120 ml of ethyl acetate are added dropwise. The mixture is left to warm to ambient temperature and washed three times with 2 N sulfuric acid and once with water. The ethyl acetate phase is then dried over sodium sulfate and chromatographed on silica gel (hexane/ethyl acetate: 5+1).

Yield: 4.5 g of 1-(2-fluoro-5-trifluoromethylphenyl)-cyclopropyl-carbaldehyde.

3-[1-(2-Fluoro-5-trifluoromethylphenyl)-cyclopropyl]-2-oxo-propionic acid

To a solution of 5.0 g 2-diethylphosphono-2-ethoxyacetic acid ethyl ester in 40 ml tetrahydrofurane, 10 ml of a 2 M solution of lithiumdiisopropylamide in tetrahydrofurane/heptane/toluene are added within 20 min. under ice cooling. The mixture is stirred for 30 min. at 0° C. Within 30 min., a solution of 4 g of 1-(2-fluoro-5-trifluoromethylphenyl)-cyclopropyl-carbaldehyde in 30 ml tetrahydrofurane is added, dropwise at 0° C. After 20 hours at ambient temperature, 2 N sulfuric acid is added to the mixture, it is then extracted with ethyl acetate, dried over sodium sulfate and concentrated. The crude product is dissolved in 50 ml ethanol and saponified with 33 ml of a 2 M sodium hydroxide solution.

Yield: 5.2 g of the acid, which is heated under reflux together with 180 ml of 2 N sulfuric acid for several hours under vigorous stirring. After extraction with ethyl acetate and washing with water, 4.6 g of 3-[1-(2-fluoro-5-trifluoromethylphenyl)-cyclopropyl]-2-oxo-propionic acid are obtained as a yellow oil.

5-{3-[1-(2-Fluoro-5-trifluoromethylphenyl)-cyclopropyl]-2-oxo-propionylamino}-phthalide At −10° C., 0.84 ml of thionyl chloride are added to 2.9 g of 3-[1-(2-fluoro-5-trifluoromethylphenyl)-cyclopropyl]-2-oxo-propionic acid in 15 ml dimethylacetamide. The mixture is stirred for 30 min. at −10° C. and for 1 hour at 0° C. and then added to 1.95 g of 5-aminophthalide (or, vice versa, 5-aminophthalide may be added to the mixture). After 16 hours at ambient temperature, 2 M hydrochloric acid and ethyl acetate are added, the organic phase is washed to neutral with water, dried over sodium sulfate and concentrated. After chromatography on silica gel (hexane/ethyl acetate: 1+1) and recrystallization from diisopropyl ether, 2.4 g of 5-{3-[1-(2-fluoro-5-trifluoromethylphenyl)-cyclopropyl]-2-oxo-propionylamino}-phthalide (m.p. 168° C.) are obtained.

(±)-5-{2-Hydroxy-3-[1-(2-fluoro-5-trifluoromethylphenyl)-cyclopropyl]-2-trifluoromethyl-propriony-lamino}-phthalide ((+)-1)

2.7 g of 5-{3-[1-(2-fluoro-5-trifluoromethylphenyl)-cyclopropyl]-2-oxo-propionylamino}-phthalide are dissolved in 15 ml dimethylformamide; 4.25 ml of trifluoromethyl-trimethylsilane and 972 g of cesium carbonate are added under ice cooling. After stirring the mixture for 18 hours at ambient temperature, 6.5 ml of a 1 M solution of tetrabutylammoniumfluoride in tetrahydrofurane are added under ice cooling and the resulting mixture is stirred for one hour. After complete addition of water it is extracted with ethyl acetate, the organic phase is dried over sodium sulfate and concentrated. After chromatography on silica gel (hexane/ethyl acetate: 3+2), 760 mg of starting material is obtained as fraction 1 and 880 mg of (±)-5-{2-hydroxy-3-[1-(2-fluoro-5-trifluoromethylphenyl)-cyclopropyl]-2-trifluoromethyl-proprionylamino}-phthalide ((±)-1) (m.p. 158° C.) is obtained as fraction 2.

Separation of Enantiomers of Compound ((±)-1):

The mixture of enantiomers of compound ((±)-1) is separated by chromatography over a chiral carrier (CHIRALPAK AD®, obtained from DAICEL) and hexane/ethanol: 97+3 as a liquid phase; 2.4 g of racemate yield:

(+)-5-{2-Hydroxy-3-[1-(2-fluoro-5-trifluoromethylphenyl)-cyclopropyl]-2-trifluoromethyl-proprionylamino}-phthalide ((+)-1) as a first fraction: 867 mg; m.p. 162-163° C., $\alpha_D$=+114.5° (c=0.5 in chloroform) and
(−)-5-{2-hydroxy-3-[1-(2-fluoro-5-trifluoromethylphenyl)-cyclopropyl]-2-trifluoromethyl-proprionylamino}-phthalide ((−)-1) as a second fraction: 860 mg; m.p. 163-164° C., $\alpha_D$=−113.7 (c=0.5 in chloroform).

b) Preparation of (±)-, (−)- and (+)-6-{2-hydroxy-3-[1-(2-fluoro-3-trifluoromethyl-phenyl)-cyclopropyl]-2-trifluoromethyl-propionylamino}-4-methyl-2,3-benzoxazin-1-one ((±)-, (+)-, (−)-2):

1-(2-Fluoro-3-trifluoromethylphenyl)-cyclopropyl-carbonitrile

Preparation from (2-fluoro-3-trifluoromethylphenyl)-acetonitrile analogously to the preparation of 1-(2-fluoro-5-trifluoromethylphenyl)-cyclopropyl-carbonitrile (cf. Example 1a)). B.p. 120° C./0.04 hPa.

1-(2-Fluoro-3-trifluoromethylphenyl)-cyclopropyl-carbaldehyde

Preparation from 1-(2-fluoro-3-trifluoromethylphenyl)-cyclopropyl-carbonitrile analogously to the preparation of 1-(2-fluoro-5-trifluoromethylphenyl)-cyclopropyl-carbaldehyde (cf. Example 1a)).

3-[1-(2-Fluoro-3-trifluoromethylphenyl)-cyclopropyl]-2-oxo-propionic acid

Preparation from 1-(2-fluoro-3-trifluoromethylphenyl)-cyclopropyl-carbaldehyde analogously to the preparation of 3-[1-(2-fluoro-5-trifluoromethylphenyl)-cyclopropyl]-2-oxo-propionic acid (cf. Example 1a). M.p. 177° C. (degradation).

6-{3-[1-(2-Fluoro-3-trifluoromethylphenyl)-cyclopropyl]-2-oxo-propionylamino}-4-methyl-2,3-benzoxazin-1-one Preparation from 3-[1-(2-fluoro-3-trifluoromethylphenyl)-cyclopropyl]-2-oxo-propionic acid analogously to the preparation of 6-{3-[1-(3-trifluoromethylphenyl)-cyclopropyl]-2-oxo-propionylamino}-4-methyl-2,3-benzoxazin-1-one (cf. Example 1c)). M.p. 117-118° C.

(±)-6-{2-Hydroxy-3-[1-(2-fluoro-3-trifluoromethylphenyl)-cyclopropyl]-2-trifluoromethyl-propionylamino}-4-methyl-2,3-benzoxazin-1-one ((±)-2)

Analogously to compound ((±)-1) in Example 1a), (±)-6-{2-hydroxy-3-[1-(2-fluoro-3-trifluoromethylphenyl)-cyclopropyl]-2-trifluoromethyl-propionylamino}-4-methyl-2,3-benzoxazin-1-one ((±)-2) is obtained from 6-{3-[1-(2-fluoro-3-trifluoromethylphenyl)-cyclopropyl]-2-oxo-propionylamino}-4-methyl-2,3-benzoxazin-1-one. M.p. 200-201° C.

Separation of Enantiomers of Compound ((±)-2):
The (+) and (−) enantiomers are separated as described in Example 1a). The separation yields:
(−)-6-{2-Hydroxy-3-[1-(2-fluoro-3-trifluoromethylphenyl)-cyclopropyl]-2-trifluoromethyl-propionylamino}-4-methyl-2,3-benzoxazin-1-one ((−)-2) as a first fraction; m.p. 171-173° C., $\alpha_D$=−115.2° (c=0.5 in chloroform), and
(+)-6-{2-hydroxy-3-[1-(2-fluoro-3-trifluoromethylphenyl)-cyclopropyl]-2-trifluoro-methyl-propionylamino}-4-methyl-2,3-benzoxazin-1-one ((+)-2) as a second fraction; m.p. 168-173° C.

c) Preparation of (±)-, (+)- and (−)-6-{2-hydroxy-3-[1-(3-trifluoromethylphenyl)-cyclopropyl]-2-methyl-propionylamino}-4-methyl-2,3-benzoxazin-1-one ((±)-, (+)- and (−)-3):

6-{3-[1-(3-Trifluoromethylphenyl)-cyclopropyl]-2-oxo-propionylamino}-4-methyl-2,3-benzoxazin-1-one 1.8 ml Thionylchloride are added at −10° C. to 6.0 g of 3-[1-(3-trifluoromethylphenyl)-cyclopropyl]-2-oxo-propionic acid (prepared as described in WO 98/54159) in 60 ml of dimethyl acetamide. The mixture is stirred for 30 min. at −10° C. and for 1 hour at 0° C. and then admixed to 5 g of 6-amino-4-methyl-2,3-benzoxazin-1-one. After 16 hours at ambient temperature, the phases are separated between water and ethyl acetate. The organic phase is washed with brine, dried over sodium sulfate and concentrated. After chromatography on silica gel using hexane and ethyl acetate (10-20%) as a liquid phase, 6.78 g of 6-{3-[1-(3-trifluoromethylphenyl)-cyclopropyl]-2-oxo-propionylamino}-4-methyl-2,3-benzoxazin-1-one are obtained (m.p. 136-139° C.).

(±)-6-{2-Hydroxy-3-[1-(3-trifluoromethylphenyl)-cyclopropyl]-2-methyl-propionylamino}-4-methyl-2,3-benzoxazin-1-one ((±)-3)

215 mg of 6-{3-[1-(3-trifluoromethylphenyl)-cyclopropyl]-2-oxo-propionylamino}-4-methyl-2,3-benzoxazin-1-one are dissolved in 7.5 dry tetrahydrofurane. Under ice cooling, 0.32 ml of a 3 M solution of methyl magnesium bromide in ether are added. After 30 min. at 0° C., the reaction mixture is poured onto a saturated ammonium chloride solution and extracted with ethyl acetate. The organic phase is washed with brine, dried over sodium sulfate and evaporated. After chromatography on silica gel using hexane and ethyl acetate (0-20%) as a liquid phase, 80 mg of starting material is obtained as fraction 1 and 95 mg of 6-{2-hydroxy-3-[1-(3-trifluoromethylphenyl)-cyclopropyl]-2-methyl-propionylamino}-4-methyl-2,3-benzoxazin-1-one ((±)-(3), m.p. 75-76° C.) is obtained as fraction 2.

Separation of Enantiomers of Compound ((±)-3):
The (+)- and (−)-enantiomers are separated as described in example 1a) for compound ((±)-1). The separation yielded:
(−)-6-{2-Hydroxy-3-[1-(3-trifluoromethylphenyl)-cyclopropyl]-2-methyl-propionylamino}-4-methyl-2,3-benzoxazin-1-one ((−)-3) as a first fraction; m.p. 129-130° C., $\alpha_D$=−54.8 (c=0.5 in chloroform), and
(+)-6-{2-hydroxy-3-[1-(3-trifluoromethylphenyl)-cyclopropyl]-2-methyl-propionylamino}-4-methyl-2,3-benzoxazin-1-one ((+)-3) as a second fraction; m.p. 132-135° C., $\alpha_D$=+55.2 (c=0.5 in chloroform).

d) Preparation of (±)-, (+)- and (−)-5-{2-hydroxy-3-[1-(2-fluoro-3-trifluoromethylphenyl)-cyclopropyl]-2-trifluoromethyl-propionylamino}-phthalide ((±)-(+)- and (−)-4):

1-(2-Fluoro-3-trifluoromethylphenyl)-cyclopropyl-carbonitrile

Preparation from (2-fluoro-3-trifluoromethylphenyl)-acetonitrile analogously to the preparation of 1-(2-fluoro-5-trifluoromethylphenyl)-cyclopropyl-carbonitrile (cf. Example 1a)). B.p. 120° C./0.04 hPa.

1-(2-Fluoro-3-trifluoromethylphenyl)-cyclopropyl-carbaldehyde

Preparation from 1-(2-fluoro-3-trifluoromethylphenyl)-cyclopropyl-carbonitrile analogously to the preparation of 1-(2-fluoro-5-trifluoromethylphenyl)-cyclopropyl-carbaldehyde (cf. Example 1a)).

3-[1-(2-Fluoro-3-trifluoromethylphenyl)-cyclopropyl]-2-oxo-propionic acid

Preparation from 1-(2-fluoro-3-trifluoromethylphenyl)-cyclopropyl-carbaldehyde analogously to the preparation of 3-[1-(2-fluoro-5-trifluoromethylphenyl)-cyclopropyl]-2-oxo-propionic acid (cf. Example 1a). M.p. 177° C. (degradation).

5-[3-[1-{2-Fluoro-3-trifluoromethylphenyl)-cyclopropyl]-2-oxo-propionylamino}-phthalide Preparation from 3-[1-(2-fluoro-3-trifluoromethylphenyl)-cyclopropyl]-2-oxo-propionic acid and 5-aminophthalide analogously to the preparation of 5-{3-[1-(2-fluoro-5-trifluoromethylphenyl)-cyclopropyl]-2-oxo-propionylamino}-phthalide (cf. Example 1a)). M.p. 157-158° C.

(±)-5-{2-Hydroxy-3-[1-(2-fluoro-3-trifluoromethylphenyl)-cyclopropyl]-2-trifluoromethyl-propionylamino}-phthalide ((±)-4)

Analogously to the preparation of compound ((±)-1) in Example 1a), (±)5-{2-hydroxy-3-[1-(2-fluoro-3-trifluoromethylphenyl)-cyclopropyl]-2-trifluoromethyl-propionylamino}-phthalide ((±)-4) is obtained from 5-{3-[1-(2-fluoro-3-trifluoromethylphenyl)-cyclopropyl]-2-oxo-propionylamino}-phthalide. M.p. 212-214° C.

Separation of Enantiomers of Compound ((±)-4):

The (+) and (−) enantiomers are separated as described in Example 1a) for compound ((±)-1). The separation yielded:
(−)-5-{2-Hydroxy-3-3-[1-(2-fluoro-3-trifluoromethylphenyl)-cyclopropyl]-2-trifluoromethyl-propionylamino}-phthalide ((−)-4) as a first fraction; m.p. 165-166° C., $\alpha_D = -115.5$ (c=0.5 in chloroform), and
(+)-5-{2-hydroxy-3-[1-(2-fluoro-3-trifluoromethylphenyl)-cyclopropyl]-2-trifluoromethyl-propionylamino}-phthalide ((+)-4) as a second fraction; m.p. 164-166° C.

Example 2

In Vivo Test on Progestogenic Activity—Ovulation Inhibition

Before the treatment is started, two menstrual cycles of female rats (weight: 190 to 210 g) were monitored. Only animals having a regular 4 day-cycle are used for the subsequent test. Starting in the metoestrus, the test compound is administered for 4 days (day 1 to 4) and the cycle is controlled thereafter.

For subcutaneous application, the test compounds are dissolved in benzyl benzoate/castor oil (1+9 v/v) and the daily dose is administered in a volume of 1 ml/kg body weight.

For peroral application, the test compounds are suspended in a carrier liquid (85 mg Myrj$^R$ in 100 ml 0.9% w/v NaCl solution) and the daily dose is administered in a volume of 2 ml/kg body weight.

Evaluation:

On day 4, after the application of the test compound, those animals having estrus or metoestrus are ovariectomized under ether anesthesia on one side. Preparations of the tubes are prepared and they are investigated for ova by means of microscope. On day 5 all animals (intact and partly ovariectomized) are killed with carbon dioxide, the tubes are preserved and analyzed in the same way. It is then determined, as a percentage, in how many animals ovulation was inhibited. Tables 1-a and 1-b below clearly show that in adult female rats, compound ((+)-l) efficiently inhibited ovulation by suppressing LH secretion. Table 1-a demonstrates that the $EC_{50}$ value for ((+)-1) is 45 µg/kg. Accordingly, this compound is to be regarded as having strong, progestational activity. A comparison with the standard progestin R5020 (promegestone) revealed that in vivo compound ((+)-l) is one of the most potent progestins identified so far, as it is by a factor of 1 to 2 (more) effective as/than R5020 (cf Table 1-b).

TABLE 1-a

| Dose [µg/kg] of ((+)−1) | % Inhibition | $EC_{50}$ [µg/kg] |
|---|---|---|
| 0 | 0 | |
| 10 | 0 | |
| 30 | 14 | |
| 100 | 100 | 45 |

TABLE 1-b

| | R5020 (=standard) | ((+)−1) | ((+)−1) (factor compared to R5020) |
|---|---|---|---|
| Ovulation Inhibition (rat) [$EC_{50}$] | 0.06 mg/kg | 0.04 mg/kg | 1-2 |

Example 3

In Vivo Test on Breast/Uterus Selectivity a) Bioassay on Proliferating/Differentiating Effects in the Rat Mammary Epithelium The object of this test is to evaluate the effect of progestins on the development of the mammary gland, in particular on the formation of terminal end-buds in the mammary gland in estrogen primed rats. Progestins together with other hormones (prolactin, estrogens, glucocorticoids, growth hormones etc.) induce proliferation and differentiation of the mammary glandular epithelium. In particular, they are involved in the morphogenesis of alveolar and terminal end buds, the sites of milk protein production and secretion into the ductal lumen.

In order to determine the effects of test progestins according to the present invention, in particular compound ((+)-1), in mammary gland differentiation and proliferation, premature female rats (Wistar Han, SPF) are ovariectomized at the age of 21 days, 4 to 6 days before treatment start. The animals are treated for 6 days with standard estrogen (estrone (E1), 70 μg/kg) and the test progestin ((+)-1) (application volume: 0.1 ml/50 g body weight; vehicle: benzyl-benzoate/castor oil (1+4 v/v); subcutaneous). Control groups are e.g.: vehicle, estrone without progestin, estradiol together with a known progestin, e.g. R5020 (promegestone). After the 6-day treatment the animals are killed with carbon dioxide.

For the whole mount staining, animals are shaved in the left abdominal inguinal mammary region, which is cut from the body together with the skin. For the histological/immunohistochemical analyses the right abdominal inguinal mammary gland is cut from the body together with the connective-tissue adhered thereto and fixed in 3.7% formalin in PBS (phosphate buffer saline; without $Ca^{2+}/Mg^{2+}$).

Whole Mount Staining:

The preparations are fixed over night in alcohol-formalin according to the method of Tellyesniczky (see below). Then the mammary gland tissue and subcutis adhered thereto are stripped from the cutis and the preparations are again fixed over night. The further steps are as follows: ethanol 70%: 1.5 hours; acetone: 3×1.5 hours; acetone: over night; isopropanol: 1.5 hours; ethanol 96%: 2 hours; hematoxylin-iron: 3 hours; VE water: first rinse the preparations and then 2×0.5 hours; ethanol 70%: over night; ethanol 80%: 1.5 hours; ethanol 96%: 1.5 hours; isopropanol: 1.5 hours. The preparations are then moved to petri dishes and left in toluene for approximately 1 hour, i.e. until they have stopped to swim up. Then the preparations are treated with cedarwood oil (Merck, no. 1.06965). The incubation times above are minimum times and can be extended. In particular, incubation in ethanol 70% after fixation can be extended to at least 2.5 weeks.

Preparation of the solutions necessary for the whole mount staining:
  a) Alcohol-formalin according to Tellyesniczky: formaldehyde 37%: 81.8 ml, ethanol 70%: 1636 ml, glacial acetic acid (to be added shortly before use): 81.8 ml (total: 1800 ml).
  b) Hematoxylin mother solution: Hematoxylin (Merck, no. 1.15938): 10 g, ethanol 96%: 100 ml. The solution must stand for 48 hours at 37° C. before use. It can be kept in a dark place for almost unlimited time.
  c) Hematoxylin-iron solution for use: hematoxylin mother solution (filtered): 15.2 ml, ethanol 96%: 1374 ml, $FeCl_3 \times 6H_2O$ (s. 4): 91.1 ml, 1 mol/l HCl: 220 ml (total: 1700 ml); adjustment to a pH of 1.25 with 2 mol/1 NaOH.
  d) $FeCl_3 \times 6H_2O$ solution: $FeCl_3 \times 6H_2O$ (Merck, no. 1.03943): 1.07 g, VE water:
  90.2 ml, HCl: 37%: 0.92 ml (total: 91.1 ml).

By means of a 40-fold magnification, the terminal end buds near the nipple in direction of the tail are counted. The area to be investigated should be about 1.8 $mm^2$. For well-differentiated preparations this area may be reduced, with at least 250 buds to be counted. After counting, the number of end buds per 1 $mm^2$ is calculated.

Figure 3:
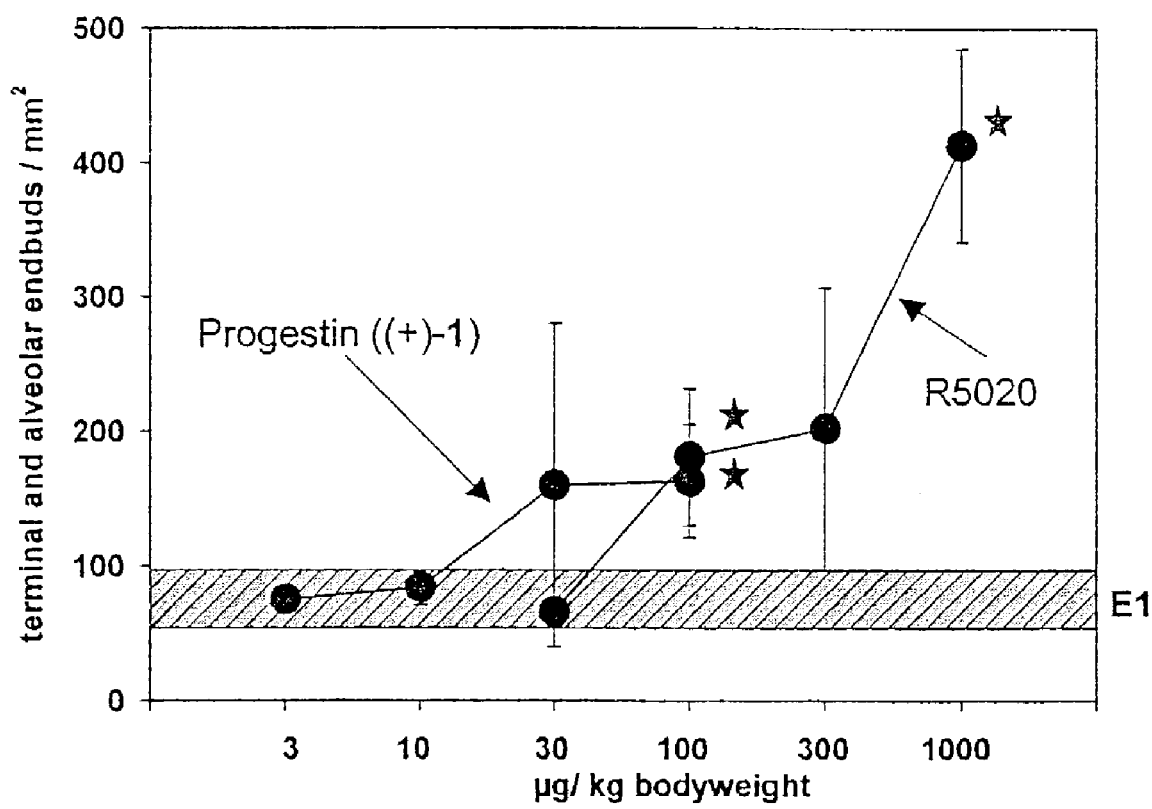
FIG. 3 relates to the stimulation of terminal and alveolar endbud formation by R5020 (the standard progestin) and compound ((+)-1) after subcutaneous application in immature ovariectomized female rats (threshold value).

Evaluation:

The number of terminal and alveolar endbuds is counted per $mm^2$ +/− standard deviation (SD). The progestagenic effect of a test progestin is either determined as a threshold value for the formation of terminal and alveolar endbuds (cf. FIG. 3) (i.e., the concentration at which a significant progestagenic effect is recognized for the first time), or as the equiefficient dose that is required to achieve a differentiation equal to 0.3 mg/kg of the reference compound promegestone (R5020) (cf. FIG. 1). Regarding the data represented in FIG. 1, differences among the various test groups are tested by ANOVA (Dunn's method). In FIG. 3, differences among the groups are tested by the t-test versus the estrone control group. In both FIG. 1 and FIG. 3, the asterisks indicate a significant difference.

MIB-5 Immunohistochemistry (According to C. Gerlach et al., Lab. Invest. 1997, 77(6), 697-698, With Modifications):

For a more detailed evaluation of the proliferation of the mammary epithelium, cells are stained with the proliferation marker MIB-5 as follows (cf. FIG. 2): Mammary glands are fixed in 4% formaldehyde/PBS for 24 h and embedded in paraffin. 4 μm sections are spread on slides, deparaffinized, treated with microwaves for 10 min. in citrate buffer pH 6.0 and rinsed with PBS. Slides are then blocked with 3% $H_2O_2$/methanol for 15 min., Blockingkit (Vektor, no. SP-2001) for 10 min. and rat serum (Sigma, no. S-7648) diluted 1:2 in PBS for 30 min to reduce nonspecific staining and rinsed in PBS. Slides are incubated for 1 hour with monoclonal antibody MIB-5 (Dianova, no. Dia-5055), which is specific for the rat Ki-67 antigen (1:200 diluted in PBS/0.2% BSA). Then, slides are washed twice in PBS/0.2% TWEEN 20, incubated with biotinylated rat anti-mouse secondary antibodies (Dianova, no. 425-066-100), diluted 1:200 in PBS/0.2% TWEEN 20 for 1 hour and washed again twice in PBS/0.2% TWEEN 20, following an incubation with avidin-biotin-peroxidase complexes (Vecstain Elite ABC Kit no. PK-6100) for 1 h. Staining is performed by means of diaminobenzidine (Zymed Substrate Kit). All steps are performed at room temperature.

Figure 2:
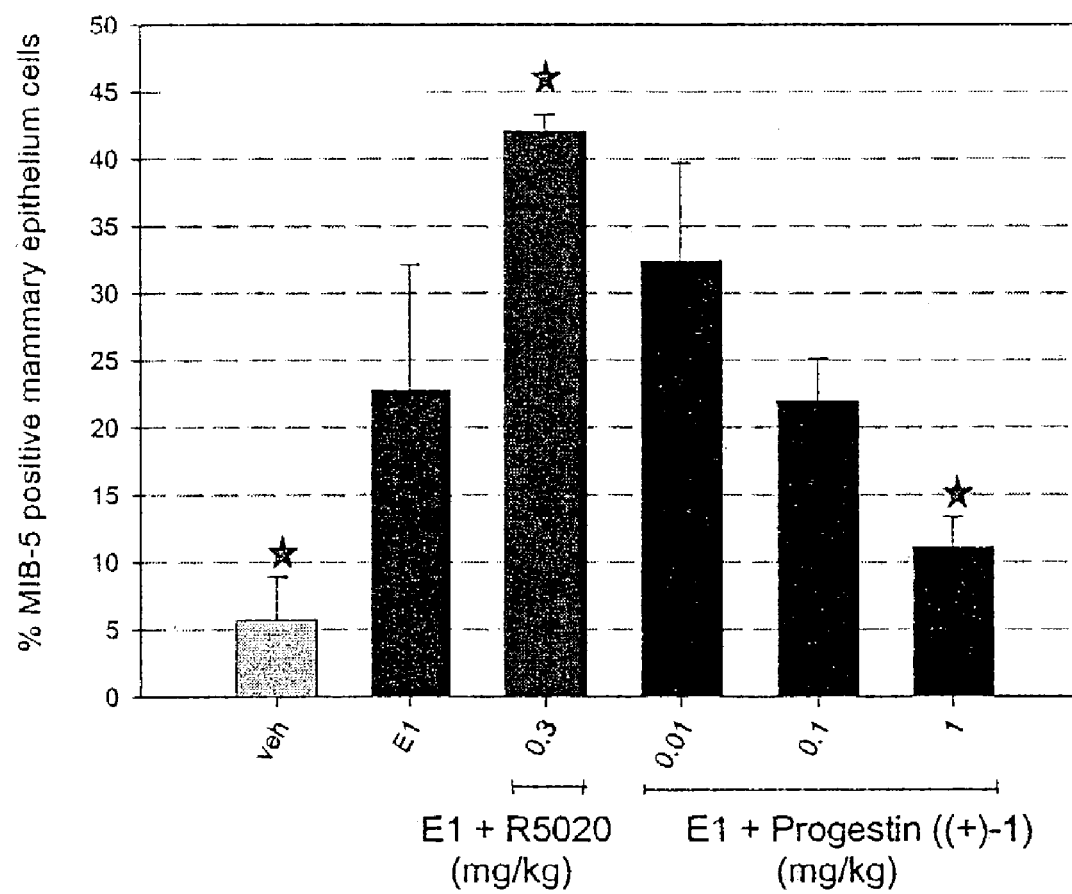
FIG. 2 shows the stimulation of the proliferation of the mammary epithelium of immature ovariectomized female rats effected by compound ((+)-1) in comparison with the standard progestin R5020 by means of MIB-5 staining.

Evaluation:

In order to characterize a test compound, the percentage of MIB-5 stained mammary epithelium cells is determined. FIG. 2 shows the percentage of MIB-5 positive epithelial cells +/− standard deviation (SD). Differences among the groups are tested by the ANOVA (Bonferroni t-test). The asterisks in FIG. 2 indicate a significant difference (p<0.05). The results of the tests are further discussed below in c).

b) Pregnancy Maintenance Test in Rat

In rats, castration induces termination of pregnancy. Progestins (combined with estrogens) are capable of maintaining pregnancy in castrated animals. However, the degree of pregnancy maintenance in castrated rats is optimal only in a defined dose range. Therefore, higher as well as lower doses generally induce a weaker effect. Accompanying treatment with defined doses of estrone ($E_1$) increases the pregnancy maintaining effect of progestins.

Pregnant rats (Wistar Han, SPF) of 190 to 220 g (5 to 8 animals per dose) are ovariectomized on day 8 of pregnancy, 2 hours after the first substance administration. From day 8 to day 14, rats are daily treated with test progestin in combination with a standard dose of $E_1$. One day later, animals are killed with carbon dioxide. For each animal, the number of living and dead fetuses is determined according to the heartbeat of the embryos. In case of empty uteri, the number of implantation sites is determined by means of staining with a 10% ammonium sulfide solution.

Formulation and Application of Test Progestins and Estrone:

S.c. (subcutaneous) application: The test progestin is dissolved in benzyl benzoate/castor oil (1+4 v/v), and the daily dose is administered in a volume of 1 ml/kg body weight.

P.o. (peroral) application: The test progestin is suspended in a carrier liquid (85 mg Myrj$^R$ in 100 ml 0.9% w/v NaCl solution), and the daily dose is administered in a volume of 2 ml/kg body weight.

I.p. (intraperitoneal) application: The test progestin is dissolved in propylene glycol and charged in miniature osmotic pumps (type 2001, 1.0 µl/h, 7 days), which are placed in the abdominal cavity of the rat.

The standard dose of estrone is 0.005 mg/kg body weight s.c. and is dissolved in benzyl benzoate/castor oil (1.4 v/v).

Evaluation:

It is determined the pregnancy maintenance per animal [%], the pregnancy maintenance per dose (median of single values) and the $EC_{50}$ (dose, at which pregnancy is maintained in 50% of the animals; 100% corresponds to control animals that are not ovariectomized). The results of the test are further discussed below in c).

c) Results Obtained for (+)-5-{2-hydroxy-3-1-(2-fluro-5-trifluoromethyl-phenyl)-cyclopropyl]-2-trifluoromethyl-propionylamino}-phthalide ((+)-1) and discussion of results The following results (Table 2) have been obtained in the bioassay on proliferating/differentiating effects in the rat mammary epithelium (whole mount staining) described under a) above and in the pregnancy maintenance test described under b) above for the most preferred compound according to the present invention, i.e. (+)-5-{2-hydroxy-3-[11-(2-fluoro-5-trifluoromethylphenyl)-cyclopropyl]-2-trifluoromethyl-propionylamino}-phthalide ((+)-1) in comparison to the standard progestin R5020 (promegestone).

Table 2 shows the dose of test progestin (either R5020 or ((+)-1)) needed per kg body weight (rat) for achieving the $EC_{50}$ value in the pregnancy maintenance test and the dose required in the bioassay on proliferation/differentiation of the mammary epithelium (rat; whole mount staining). "Equi-efficient dose" means that the middle column shows the dose of ((+)-1) needed to achieve the same effect as achieved e.g. with 0.3 mg/kg R5020. The far right column shows the factor the test progestin ((+)-1) differs from the standard progestin R5020 regarding its activity in both tests. The different pairs of values entered for the test on the differentiation/proliferation of the mammary epithelium stem from three different tests performed independently. The median of the single values results in a factor (cf. the far left column) of ca. 1.

TABLE 2

|  | R5020 (=standard) | ((+)-1) | ((+)-1) (factor compared to R5020) |
|---|---|---|---|
| Maintenance of pregnancy (rat) [EC$_{50}$] | 0.1 mg/kg/d | 0.012 mg/kg/d | 8 |
| Mammary gland, whole mount staining (rat) [equi-efficient dose] | 0.3 mg/kg/d | 0.6 mg/kg/d | ca. 1 |
|  | 0.3 mg/kg/d | 0.9 mg/kg/d |  |
|  | 0.1 mg/kg/d | 0.03 mg/kg/d |  |
| Mammary gland, whole mount staining (rat) [threshold value] |  | 0.1 mg/kg/d |  |

The preferred progestin according to the present invention, compound ((+)-1), induces a dose-dependent increase of terminal and alveolar endbuds, with an equiefficient dose to 0.3 mg/kg/d promegestone of 0.6 mg/kg/d (FIG. 1).

Furthermore, the threshold value for ((+)-1) for the induction of terminal and alveolar endbuds is 100 µg/kg/d (see FIG. 3). Interestingly, there is a dose-dependent decrease of MIB-5 positive cells with increasing concentrations of ((+)-1) (FIG. 2). FIG. 2 furthermore demonstrates that 0.3 mg/kg/d promegestone show ~42% of MIB-5 positive cells, whereas 1 mg/kg/d ((+)-1) shows ~12% of MIB-5 positive cells.

Taken together, these results indicate that ((+)-1) exhibits approximately the same activity on the mammary gland as the reference compound promegestone. Most noteworthy is that at doses where pregnancy is fully maintained (cf. Table 2), no effects on terminal and alveolar end bud formation can be observed (FIG. 3, Table 2). Thus, ((+)-1) shows tissue-selective activity on the uterus versus the mammary gland. This dissociation in favor of uterotropic activity is at least six fold. Furthermore, there is an inverse correlation of the dose of ((+)-1) and the induction of proliferation of the mammary gland.

The above results clearly indicate that the preferred compound according to the present invention, (+)-5-{2-hydroxy-3-[1-(2-fluoro-5-trifluoromethylphenyl)-cyclopropyl]-2-trifluoromethyl-propionylamino}-phthalide ((+)-1), is very potent in the maintenance of pregnancy, while its proliferating/differentiating effects on the mammary epithelium are extremely low when compared with the standard progestin R5020: Compared to R5020, compound ((+)-1) is eight times as potent regarding maintenance of pregnancy, but about equally as potent as R5020 at the mammary gland. These results impressively demonstrate that compound ((+)-1) is a selective modulator of PR mediated effects according to the present invention in that it enhances PR mediated effects (maintenance of pregnancy) in the uterus, i.e., the first selected target tissue according to the present invention, relative to PR mediated effects (proliferation/differentiation of the mammary gland) in the breast, i.e., the second selected target tissue according to the present invention. In particular, as indicated above, when compound ((+)-1) is administered in an amount which is sufficient for maintaining pregnancy, no effects at the mammary gland are observed (see Table 2 and FIG. 3). Thus, this compound is particularly suitable for use in contraception, HRT and in the treatment of gynecological disorders as outlined above in the section "Detailed Description of the Invention". The preferred progestin according to the present invention, compound ((+)-1), is especially suitable for use in estrogen-free oral contraceptives.

The above results obtained for compound ((+)-1) regarding its uterus/breast dissociated activity profile not only demonstrate that this compound is highly suitable as a tissue-specific progestin according to the present invention for the indications and applications mentioned in the section "Detailed description of the invention", but they also demonstrate the viability of the concept that PR isoform specificity of PR ligands is connected to tissue-specificity of PR ligands, cf. PCT/EP01/15200 (US No. 60/305,875). Furthermore, the results show that tissue-specific progestins, in particular uterus/breast selective progestins according to the present invention may be identified by identifying progestins that are PR isoform, i.e., PR-A versus PR-B, selective. The above results specifically demonstrate that progestins with a selectivity for PR isoform A compared to PR isoform B as demonstrated below in Example 5 selectively enhance PR mediated effects in the uterus with respect to PR mediated effects in the breast at doses suitable for the maintenance of pregnancy (cf. above Table 2). However, it is to be understood that PR-A versus PR-B selectivity (which has been determined for the progestins according to the present invention as demonstrated in Example 5 below)

does not exclusively result in uterus/breast selectivity (as it was confirmed above for the progestins of the present invention), but that any other progesterone target tissue selectivity and any other selective modulation of PR mediated effects based on progesterone isoform mediated effects may be involved.

Example 4

In Vivo Test on Oral Protestational Activity—Endometrial Transformation in Rabbit The test is performed in juvenile female rabbits (New Zealand white, 30 to 35 days old; obtained from Schriever, Germany). From days 1 to 4, all rabbits are primed with 5.0 g/kg/day 17α-estradiol (s.c., 0.5 ml/kg/day) in order to induce proliferation of the endometrium. From days 7 to 10, the test compound is applied orally (p.o., 0.5 ml/kg/day) at doses of 0.001, 0.01 and 0.1 mg/kg/day. A group which receives only vehicle after estradiol priming serves as a negative control. A second group which receives only progesterone in order to induce endometrial differentiation after estradiol priming is used as a positive control. In order to study the progestagenic activity of ((+)-1), which is the most preferred compound according to the present invention, one treatment group-receives only the compound ((+)-1) after estradiol priming.

Evaluation:

Autopsy is performed on day 1. As a parameter for progestagenic activity, the McPhail index (i.e., the degree of differentiation) is determined by means of light microscopy (scores: 1 to 4; 1=no glandular differentiation, 4=maximal differentiation).

As demonstrated below in Table 3, the preferred compound according to the present invention, compound ((+)-1), is highly potent in the endometrial transformation test in rabbit (Clauberg test). An identical potency is determined for ((+)-1) upon subcutaneous as well as oral application. Thus, compound ((+)-1) must be considered to be highly active when administered orally.

TABLE 3

| Mode of Application | ((+)-1) [mg/kg] | McPhail Index | Threshold Value [mg/kg] |
|---|---|---|---|
| Subcutaneous (s.c.) | 0.001 | 1.0 | 0.001-0.01 |
|  | 0.01 | 2.7 |  |
|  | 0.1 | 3.8 |  |
| Oral (p.o.) | 0.001 | 1.2 | 0.001-0.01 |
|  | 0.01 | 2.5 |  |
|  | 0.1 | 3.0 |  |

Example 5

In Vitro Test on PR-A/PR-B Isoform Specificity

According to the eighth and ninth aspects of the present invention, the progestins of general formula (I), however including the compound 5-[3-{1-(3-trifluoromethylphenyl)-cyclopropyl}-2-hydroxy-2-trifluoromethylpropionylamino]-phthalide excluded from the first, second, third, fourth and sixth aspects of the invention, are useful for selectively activating PR-A transcription with respect to PR-B transcription, i.e. the progestins of the present invention preferably do not activate PR-B transcription, at least not to the same degree as PR-A transcription. Accordingly, these progestins are useful for selectively activating PR-A mediated effects with respect to PR-B mediated effects, i.e., these compounds preferably do not influence PR-B mediated effects. In the following, an in vitro test for determining whether a certain progestin is selective for PR-A or PR-B is described. It is also demonstrated below that according to this in vitro test, the progestins of general formula (I) according to the present invention are selective PR-A agonists. Further details regarding the performance of this assay, in particular regarding the preparation of the PR-A and PR-B transfected cells, may be found in PCT/EP01/15200 (U.S. Ser. No. 60/305,875), which is herein incorporated by reference.

The method for screening for PR isoform-specific progestins according to the present invention is carried out with first and second SK-N-MC cells stably transfected with a plasmid expressing the HPR-A (first cells) or the hPR-B (second cells) and the LUC reporter gene linked to the hormonally responsive MTV promoter.

The cells are cultured in Minimum Essential Medium with Earl's Salts (S-MEM, without L-glutamine; Gibco BRL, no. 21090-022), supplemented with 10% fetal calf serum (FCS), penicillin 100U/streptomycin 100 µg/ml (Biochrom, no. A2213), L-glutamine 4 mmol/l (Gibco BRL, no. 25030-024), sodium pyruvate 1 mmol/l (Biochrom, no. L0473) and 1×non-essential amino acids (Biochrom, no. K0293) at a temperature of 37° C. and in an atmosphere of 5% carbon dioxide.

For the transcription assay, the cells are seeded onto 96-well dishes ($2\times10^4$ cells/dish) and cultured in a medium as described above, with the exception that the FCS is replaced by a 3% charcoal stripped FCS. 48 hours later, cells are contacted with prediluted test compounds. For determination of agonistic activity, cells are cultured in the presence of 6 increasing concentrations ($10^{-6}$ to $10^{-11}$ mol/l) of test progestins. As a positive control for reporter gene induction cells are treated with $10^{-6}$ to $10^{-11}$ mol/l R5020 (promegestone). As a negative control for reporter gene induction, cells are cultured in 1% ethanol.

After incubation with test progestins for 24 hours, the medium is removed and cells are lysed with 20 µl of lysis buffer (Luciferase Assay System E 153A; Promega) and under agitation of the plate for 101 min. After addition of 30 µl of luciferase reagent (Luciferase Assay System E 151A+ 152A; Promega) within 30 seconds per plate, the activity of the luciferase reporter gene product is determined in the cell lysates by means of a Microlite ML 3000 microtiter plate luminometer (Dynatech) in cycle mode.

Evaluation of the response gives the efficacy [%], and evaluation of the $EC_{50}$s values gives the potency [nM]. Calculation of the agonistic activity is conducted as follows:

The LUC activity [%] for the measured data points is calculated as follows:

$$\text{relative } LUC \text{ activity } [\%] = 100\times\frac{\text{response } 10^{-6} \text{ to } 10^{-11} \text{ mol/l test compound} - CO}{CI - CO}$$

wherein CI=100% stimulation (R5020, $10^{-7}$ mol/l) and CO=0% stimulation (ethanol, 1%).

Thus, the efficacy [%] is calculated according to:

$$\text{efficacy } [\%] = 100 \times \frac{\text{response } 10^{-7} \text{ mol/l test compound} - CO}{CI - CO}$$

The potency [nM], i.e. the $EC_{50}$, is determined graphically.

Some efficacy results achieved for different progestins according to the present invention are presented below in Table 2. These results clearly demonstrate the selectivity of the progestins of the present invention, in particular compound ((+)-1) for PR isoform A. Thus, these progestins are capable of selectively activating PR-A transcription with respect to PR-B transcription. Also, these progestins are capable of selectively enhancing PR-A mediated effects with respect to PR-B mediated effects. Thus, while the prior art always strived for more potent progestins, the present invention provides highly progesterone receptor isoform, in particular progesterone receptor A isoform selective progestins suitable for selectively targeting certain desired tissues or organs, preferably for selectively activating PR mediated effects in uterine tissue with respect to PR mediated effects in breast tissue.

TABLE 4

|  | PR-A agonism efficacy [%] | PR-B agonism efficacy [%] | Δ agonism efficacies (A-B) |
|---|---|---|---|
| (+)-5-{2-hydroxy-3-[1-(2-fluoro-5-trifluoromethylphenyl)-cyclopropyl]-2-trifluoromethyl-propionylamino}-phthalide, ((+)-1) | 88.7 | 25 | 64 |
| (+)-6-{2-hydroxy-3-[1-(2-fluoro-3-trifluoromethylphenyl)-cyclopropyl]-2-trifluoromethyl-propionylamino}-4-methyl-2,3-benzoxazin-1-one ((+)-2) | 99.2 | 67.5 | 32 |
| (+)-6-{2-hydroxy-3-[1-(3-trifluoromethylphenyl)-cyclopropyl]-2-methyl-propionylamino}-4-methyl-2,3-benzoxazin-1-one ((+)-3) | 94 | 71 | 23 |
| (+)-5-{2-hydroxy-3-[1-(2-fluoro-3-trifluoromethylphenyl)-cyclopropyl]-2-trifluoromethyl-propionylamino}-phthalide ((+)-4) | 100 | 82 | 18 |

Example 6

Antiuterotropic Activity in the Rat

Compounds with estrogenic activity induce uterine growth, resulting in an increase in uterine weight. They also induce a characteristic change of the appearance of the endometrial epithelium as indicated by an increase in epithelial height. PR modulators counteract estrogenic activity by inhibiting uterine weight gain and epithelial cell proliferation. This effect is sometimes referred to as "functional antiestrogenic" effect.

Figure 4:
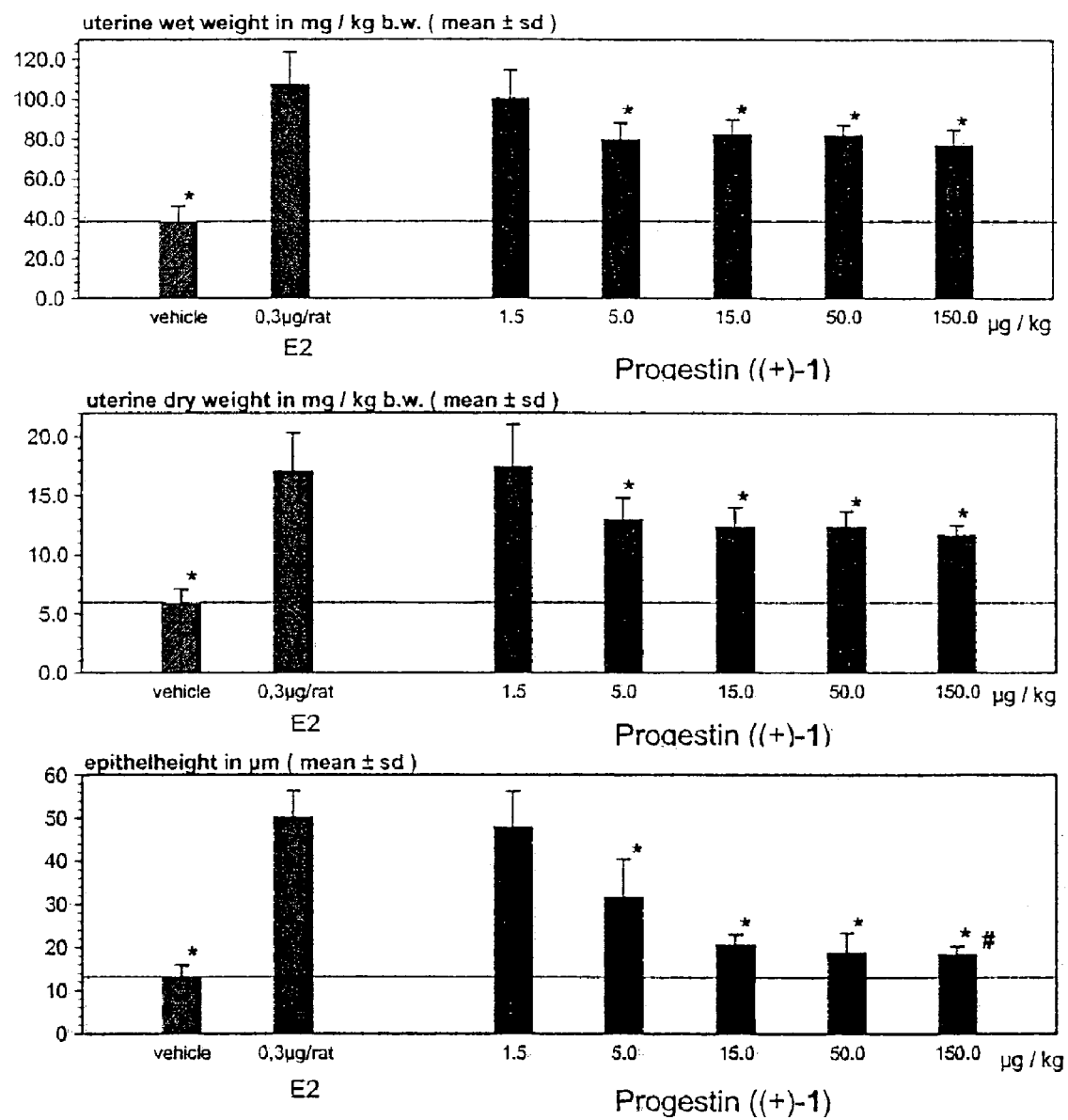
FIG. 4 demonstrates the antiestrogenic activity of compound ((+)-1) on uterine growth in the rat (uterine wet weight and uterine dry weight; epithelial height) compared to the reference group treated with estradiol.

To test for antiuterotropic activity of the most preferred progestin according to the present invention, i.e., compound ((+)-1), ovariectormized rats are treated for 3 days with 0.3 μg/kg/d estradiol (E2) and in addition with increasing doses of ((+)-1) (cf. FIG. 4). Each test group shown in FIG. 4 consists of 10 rats, with the exception of one group (cf. FIG. 4, bottom diagram, 150 μg/kg of ((+)-1)), indicated by "#"), which consists of nine rats.

Evaluation:

Changes in uterine weight, luminal epithelial height and the status of cell proliferation and keratinization of the vaginal smear servs as parameters for estrogenic activity. In combination with ((+)-1), decreases in estrogen-stimulated uterine weight gain and luminal epithelial height are parameters for antiestrogenic activity (cf. FIG. 4).

For the reference group (estradiol (E2)-treated), stimulation of the uterine weight and the luminal epithelial height in comparison to the vehicle control was calculated as follows:

$$\frac{\text{mean weight (reference compound)}}{\text{mean weight (vehicle control)}} \times 100\% = \% \text{ stimulation}$$

In the antiestrogen assay, inhibition of uterine weight or luminal epithelial height in comparison to the effect seen with the reference compound (estradiol) was calculated as follows:

$$\frac{\text{mean weight (test compound)} - \text{mean weight}(veh.\ contr.)}{\text{mean weight }(ref.\ \text{compound}) - \text{mean weight }(veh.\ contr.)} \times 100\% = \% \text{ stimulation}$$

For statistical analysis, the 95% confidence interval was calculated using a software which was developed by the Biostatistical Department of Schering AG. The asterisks indicate a significant difference ($p<0.05$).

Discussion:

((+)-1), when administered in combination with estradiol, has a strong functional antiestrogenic effect in terms of dose-dependent inhibition of uterine weight gain and epithelial cell height as shown in FIG. 4. A dose of 5 μg/kg/d of ((+)-1) shows a submaximum effect. Maximum effect is observed with a dose of 15 μg/kg/d.

In conclusion, ((+)-1) is a PR modulator with potent functional antiestrogenic activity. The antiuterotropic activity of ((+)-1) occurs in the same dose range as its pregnancy-maintaining activity ($EC_{50}$ value 12 μg/kg/d). These results demonstrate the high progestogenic potency that is exhibited by ((+)-1) in the uterus.

The threshold value of progestin ((+)-1) for the formation of terminal and alveolar endbuds in the mammary gland is very high (cf. FIG. 3 and Table 2), whereas the effects on the uterus may already be observed at a very low concentration of ((+)-1) (cf. e.g. Example 6 and FIG. 4), demonstrating the dissociated effect of this invention compound in the breast versus the uterus.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European Patent Application No. 02 005 530.7, filed Mar. 11, 2002, and U.S. Provisional Application Serial No. 60/363,044, filed Mar. 11, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound (I) which is:
   (+)-5-{2-hydroxy-3-[1-(2-fluoro-5-trifluoromethylphenyl)-cyclopropyl]-2-trifluoromethyl-propionylamino}-phthalide,
   (+)-6-{2-hydroxy-3-[1-(2-fluoro-3-trifluoromethylphenyl)-cyclopropyl]-2-trifluoromethyl-propionylamino}-4-methyl-2,3-benzoxazin-1-one,
   (+)-5-{2-hydroxy-3-[1-(2-fluoro-3-trifluoromethylphenyl)-cyclopropyl]-2-trifluoromethyl-propionylamino}-phthalide, or
   (+)-6-{2-hydroxy-3-[1-(2-fluoro-5-trifluoromethylphenyl)-cyclopropyl]-2-trifluoromethyl-propionylamino}-4-methyl-2,3-benzoxazin-1-one.

2. A compound of claim 1, which is:
   (+)-5-{2-Hydroxy-3-[1-(2-fluoro-5-trifluoromethylphenyl)-cyclopropyl]-2-trifluoromethyl-propionylamino}-phthalide, or
   (+)-6-{2-hydroxy-3-[1-(2-fluoro-5-trifluoromethylphenyl)-cyclopropyl]-2-trifluoromethyl-propionylamino}-4-methyl-2,3-benzoxazin-1-one.

3. A pharmaceutical composition comprising a compound (I) as defined in claim 1.

4. The pharmaceutical composition according to claim 3, comprising the compound:
   (+)-5-{2-hydroxy-3-[1-(2-fluoro-5-trifluoromethylphenyl)-cyclopropyl]-2-trifluoromethyl-propionylamino}-phthalide or
   (+)-6-{2-hydroxy-3-[1-(2-fluoro-5-trifluoromethylphenyl)-cyclopropyl]-2-trifluoromethyl-propionylamino}-4-methyl-2,3-benzoxazin-1-one.

5. A pharmaceutical composition comprising a compound (I) of claim 1 in an amount such that the daily dose is 0.01 to 2 mg.

6. The pharmaceutical composition of claim 4, comprising the compound (I) in an amount such that the daily dose is 0.01 to 2 mg.

7. The pharmaceutical composition of claim 3, further comprising 17α-ethinyl estradiol.

8. The pharmaceutical composition of claim 4, further comprising 17α-ethinyl estradiol.

9. The pharmaceutical composition of claim 5, further comprising 17α-ethinyl estradiol.

10. The pharmaceutical composition of claim 6, further comprising 17α-ethinyl estradiol.

11. The pharmaceutical composition according to claim 7, wherein the 17α-ethinyl estradiol is present in an amount such that the daily dose is 0.01 to 0.05 mg.

12. The pharmaceutical composition according to claim 8, wherein the 17α-ethinyl estradiol is present in an amount such that the daily dose is 0.01 to 0.05 mg.

13. The pharmaceutical composition according to claim 9, wherein the 17α-ethinyl estradiol is present in an amount such that the daily dose is 0.01 to 0.05 mg.

14. The pharmaceutical composition according to claim 10, wherein the 17α-ethinyl estradiol is present in an amount such that the daily dose is 0.01 to 0.05 mg.

15. A method for contraception, comprising administering to a female patient in need thereof an effective amount of a compound (I) of claim 1.

16. The method according to claim 15, wherein the compound (I) is administered orally.

17. The method according to claim 15, wherein the compound (I) is:
   (+)-5-{2-hydroxy-3-[1-(2-fluoro-5-trifluoromethylphenyl)-cyclopropyl]-2-trifluoromethyl-propionylamino}-phthalide, or
   (+)-6-{2-hydroxy-3-[1-(2-fluoro-5-trifluoromethylphenyl)-cyclopropyl]-2-trifluoromethyl-propionylamino}-4-methyl-2,3-benzoxazin-1-one.

18. The method according to claim 15, wherein compound (I) is administered in an amount such that the daily dose is 0.01 to 2 mg.

19. The method according to claim 17, wherein compound (I) is administered in the form of an estrogen-free oral contraceptive.

20. The method according to claim 17, wherein compound (I) is administered in an amount such that the daily dose is 0.01 to 2 mg.

21. The method according to claim 15, further comprising administering to the female patient in need thereof 17α-ethinyl estradiol.

22. The method according to claim 17, further comprising administering to the female patient in need thereof 17α-ethinyl estradiol.

23. The method according to claim 21, wherein the 17α-ethinyl estradiol is administered in an amount such that the daily dose is 0.01 to 0.05 mg.

24. The method according to claim 22, wherein the 17α-ethinyl estradiol is administered in an amount such that the daily dose is 0.01 to 0.05 mg.

25. The method according to claim 21, wherein the daily doses of the compound (I) and the 17α-ethinyl estradiol to be administered vary independently of each other over the course of the female menstrual cycle.

26. The method according to claim 22, wherein the daily doses of the compound (I) and the 17α-ethinyl estradiol to be administered vary independently of each other over the course of the female menstrual cycle.

* * * * *